(12) United States Patent
Sivakumar et al.

(10) Patent No.: US 7,276,478 B2
(45) Date of Patent: Oct. 2, 2007

(54) METHODS OF TREATING AUTOIMMUNE DISEASES USING IL-21

(75) Inventors: Pallavur V. Sivakumar, Seattle, WA (US); Andrew J. Nelson, Saint Leonard (CA)

(73) Assignee: ZymoGenetics, Inc., Seattle, WA (US)

( * ) Notice: Subject to any disclaimer, the term of this patent is extended or adjusted under 35 U.S.C. 154(b) by 274 days.

(21) Appl. No.: 10/951,239

(22) Filed: Sep. 27, 2004

(65) Prior Publication Data

US 2005/0095223 A1 May 5, 2005

Related U.S. Application Data

(60) Provisional application No. 60/505,919, filed on Sep. 25, 2003.

(51) Int. Cl.
*A61K 38/20* (2006.01)
*A61K 45/00* (2006.01)

(52) U.S. Cl. .......................... 514/12; 424/85.2
(58) Field of Classification Search ................ None
See application file for complete search history.

(56) References Cited

U.S. PATENT DOCUMENTS

| | | | |
|---|---|---|---|
| 6,057,128 A | 5/2000 | Donaldson et al. | 435/69.1 |
| 6,307,024 B1 * | 10/2001 | Novak et al. | 530/351 |
| 6,605,272 B2 | 8/2003 | Novak et al. | 424/85.2 |
| 6,686,178 B2 | 2/2004 | Novak et al. | 435/69.52 |
| 2004/0016010 A1 | 1/2004 | Carter et al. | |
| 2004/0136954 A1 | 7/2004 | Grusby et al. | |
| 2005/0193434 A1 | 9/2005 | Leonard et al. | |
| 2006/0024268 A1 | 2/2006 | Kasaian et al. | |
| 2006/0057123 A1 | 3/2006 | Ettinger al. | |
| 2006/0159655 A1 | 7/2006 | Collins et al. | |
| 2006/0177421 A1 | 8/2006 | Niels et al. | |

FOREIGN PATENT DOCUMENTS

WO 2005/067956 1/2005

OTHER PUBLICATIONS

James A. Wells, Sep. 18, 1990, Biochemistry, vol. 29, No. 37, pp. 8509-8517.*
Mehta et al. Immunological Reviews, 2004. vol. 202, pp. 84-95.*
U.S. Appl. No. 10/456,780, filed Jun. 6, 2003, Nelson et al.
U.S. Appl. No. 10/735,149, filed Dec. 12, 2003, Zamost et al.
U.S. Appl. No. 11/539,036, filed Oct. 5, 2006, Zamost et al.
U.S. Appl. No. 11/539,045, filed Oct. 5, 2006, Zamost et al.
U.S. Appl. No. 11/539,055, filed Oct. 5, 2006, Zamost et al.
U.S. Appl. No. 10/456,262, filed Jun. 6, 2003, Nelson et al.
U.S. Appl. No. 11/553,367, filed Oct. 26, 2006, Nelson et al.
U.S. Appl. No. 11/553,381, filed Oct. 26, 2006, Nelson et al.
U.S. Appl. No. 11/553,389, filed Oct. 26, 2006, Nelson et al.
U.S. Appl. No. 11/553,392, filed Oct. 26, 2006, Nelson et al.
U.S. Appl. No. 11/553,395, filed Oct. 26, 2006, Nelson et al.
U.S. Appl. No. 11/548,196, filed Oct. 10, 2006, Nelson et al.
U.S. Appl. No. 11/548,202, filed Oct. 10, 2006, Nelson et al.
U.S. Appl. No. 11/548,517, filed Oct. 11, 2006, Nelson et al.
U.S. Appl. No. 11/548,530, filed Oct. 11, 2006, Nelson et al.
U.S. Appl. No. 11/548,538, filed Oct. 11, 2006, Nelson et al.
U.S. Appl. No. 11/548,554, filed Oct. 11, 2006, Nelson et al.
U.S. Appl. No. 11/548,567, filed Oct. 11, 2006, Nelson et al.
U.S. Appl. No. 11/548,574, filed Oct. 11, 2006, Nelson et al.
U.S. Appl. No. 11/548,585, filed Oct. 11, 2006, Nelson et al.
U.S. Appl. No. 11/548,877, filed Oct. 12, 2006, Nelson et al.
U.S. Appl. No. 11/548,946, filed Oct. 12, 2006, Nelson et al.
U.S. Appl. No. 11/548,963, filed Oct. 12, 2006, Nelson et al.
U.S. Appl. No. 11/548,969, filed Oct. 12, 2006, Nelson et al.
U.S. Appl. No. 11/539,479, filed Oct. 6, 2006, Kindsvogel et al.
U.S. Appl. No. 11/539,493, filed Oct. 6, 2006, Kindsvogel et al.
U.S. Appl. No. 11/539,511, filed Oct. 6, 2006, Kindsvogel et al.
U.S. Appl. No. 11/285,970, filed Nov. 23, 2005, Yee.
U.S. Appl. No. 10/659,684, filed Sep. 10, 2003, Novak et al.
U.S. Appl. No. 11/549,772, filed Oct. 16, 2006, Novak et al.
U.S. Appl. No. 11/551,807, filed Oct. 23, 2006, Novak et al.
U.S. Appl. No. 11/551,344, filed Oct. 20, 2006, Novak et al.
U.S. Appl. No. 11/549,868, filed Oct. 16, 2006, Novak et al.
U.S. Appl. No. 11/551,356, filed Oct. 20, 2006, Novak et al.
U.S. Appl. No. 11/551,362, filed Oct. 20, 2006, Novak et al.
U.S. Appl. No. 11/551,368, filed Oct. 20, 2006, Novak et al.
U.S. Appl. No. 11/551,811, filed Oct. 23, 2006, Novak et al.
U.S. Appl. No. 11/551,820, filed Oct. 23, 2006, Novak et al.
U.S. Appl. No. 10/787,442, filed Feb. 26, 2004, Novak et al.
U.S. Appl. No. 11/532,776, filed Sep. 18, 2006, Novak et al.
U.S. Appl. No. 11/551,127, filed Oct. 19, 2006, Novak et al.
U.S. Appl. No. 11/551,136, filed Oct. 19, 2006, Novak et al.
U.S. Appl. No. 11/551,139, filed Oct. 19, 2006, Novak et al.
U.S. Appl. No. 11/551,144, filed Oct. 19, 2006, Novak et al.
U.S. Appl. No. 11/551,349, filed Oct. 20, 2006, Novak et al.
U.S. Appl. No. 11/563,928, filed Nov. 28, 2006, Sivakumar et al.
U.S. Appl. No. 11/564,001, filed Nov. 28, 2006, Sivakumar et al.
U.S. Appl. No. 11/346,580, filed Feb. 2, 2006, Novak et al.

(Continued)

*Primary Examiner*—Gary Nickol
*Assistant Examiner*—Fozia Hamud
(74) *Attorney, Agent, or Firm*—Deborah A. Sawislak

(57) ABSTRACT

Administration of IL-21 results in decreasing autoimmune responses and thereby provides a beneficial treatment for autoimmune diseases. Specific autoimmune diseases that may be treated include multiple sclerosis, rheumatoid arthritis, systemic lupus erythematosus, psoriasis, ankylosing spondilitis, scleroderma, Type I diabetes, psoriatic arthritis, osteoarthritis, inflammatory bowel disease, atopic dermatitis and asthma. Pharmaceutical compositions can include IL-21 polypeptides and active fragments thereof.

7 Claims, No Drawings

OTHER PUBLICATIONS

O'Shea et al., "A New Modality for Immunosuppression: Targeting the JAK/STAT Pathway," *Nat Rev Drug Discov.* 3(7):555-64, 2004.

Pene et al., "Cutting Edge: IL-21 is a Switch Factor for the production of IgG$_1$ and IgG$_3$ by Human B Cells," *J. Immunol.* 172(9):5144-7, 2004.

Jungel et al., "Expression of Interleukin-21 Receptor, but Not Interleukin-21, in Synovial Fibroblasts and Synovial Macrophages of Patients withRheumatoid Arthritis," *Arthritis Rheum.* 50(5):1468-76, 2004.

Ozaki et al., "Regulation of B cell differentiation and plasma cell generation by IL-21, a novel inducer of Blimp-1 and Bcl-6," *J Immunol.* 173(9):5361-71, 2004.

Gallegos et al., "Driven to Autoimmunity: the Nod Mouse," *Cell* 117(2):149-51, 2004.

Monteleone et al., "IL-21 enhances TH1 cell signaling and INF gamma production in Crohn's disease," *Gastroenterol 126*(4):, 2004.

O'Shea et al., "Jak3 and the pathogenesis of severe combined immunodeficiency," *Mol Immunol.* 727-37, 2004.

Sivakumar et al., Interleukin-21 is a T-helper cytokine that regulates humoral immunity and cell-mediated anti-tumor responses,: *Immunology 112*(2):177-82, 2004.

Distler et al., "Overexpression of IL-21 Receptor mRNA in the Epidermis of Patients with Systemic Sclerosis: Lessons from the SCID Mouse Transplantation Model," *Ann. Rheumatic Diseases 63*(S1): OP0158, 2004.

Rowshani et al., "Effects of CD25 monoclonal antibody on proliferative and effector functions of alloactivated human T cells in vitro," *Eur J Immunol.* 34(3):882-99, 2004.

Asli et al., "Roles of lymphoid cells in the differentiation of Langerhans dendritic cells in mice," *Immunobiology 209*(1-2):209-21, 2004.

Sague et al., "The Presence of IL-21 During Differentiation of Bone Marrow-Derived Dendritic Cells Inhibits Dendritic Cell Maturation," *J. Leukocyte Biol. Supp* (0):162, 2004.

Alexopoulos et al., "Tolerance Induction Using IL-21 Antagonizing Fusion Protein," *Experimental Tolerance Induction Conf.* 09(0): Abs. 101, 2004.

Brandt et al. "Interleukin-21 Inhibits Dendritic Cell-Mediated T Cell Activation and Induction of Contact Hpersensitivity In Vivo," *J. Invest. Dermatol 121*(6):1379-82, 2003.

Brandt et al., "Interleukin-21 inhibits dendritic cell activation and maturation," *Blood 102*(12):4090-8, 2003.

Distler et al., "Inflammation-independent Overexpression of IL-21 Receptor in mRNA in Keratinocytes from Patients with Systemic Sclerosis," *Am. College of Rheumatol.* Abs. Suppl. Abst. 848, 2003.

Cohen et al., "Increased expression of CD132 and multiple IL-2 family receptors in psoriasis vulgaris," *J. Investigative Dermatol.* Abst. 0115, 2003.

Cui et al. "Cytokine genetic adjuvant facilitates prophylactic intravascular DNA vaccine against acute and latent herpes simplex virus infection in mice," Ueda et al., "Expression of Functional IL-21 Receptor on adult T-cell Leukemia Cells," *Blood 102*(11), 2003.

Suto et al., "Interleukin 21 prevents antigen-induced IgE production by inhibiting germ line Cε transcription of IL-4-stimulated B cells," *Blood 100*(13):4565-73, 2002.

De Groot-Kruseman et al., "Expression of the Novel Cytokine IL-21 During Acute Rejection After Clinical Heart Transplantation and the Effect of Immunosuppressive Agents," *J. Interferon Cytokine Res.* 22(S1): abst. P-2-1, 2002.

Witek et al., "Primary Machrophages Express IL-21R and Respond to IL-21 by Proliferating and Secreting Increased Levels of Cytokines and Chemokines," abst. P-2-12, 2002.

Keane-Myers et al., "A Role for IL-21 in Mouse Models of Allergic Asthma," Keystone Symposia, Cytokines, Disease and Therapeutic Intervention, 2005.

\* cited by examiner

METHODS OF TREATING AUTOIMMUNE DISEASES USING IL-21

REFERENCE TO RELATED APPLICATIONS

This application claims the benefit of U.S. Provisional Application Ser. No. 60/505,919, filed Sep. 25, 2003, which is herein incorporated by reference.

BACKGROUND OF THE INVENTION

Cytokines generally stimulate proliferation or differentiation of cells of the hematopoietic lineage or participate in the immune and inflammatory response mechanisms of the body. The interleukins are a family of cytokines that mediate immunological responses. Central to an immune response is the T cell, which produces many cytokines and provide adaptive immunity to antigens. Cytokines produced by the T cell have been classified as type 1 and type 2 (Kelso, A. *Immun. Cell Biol.* 76:300-317, 1998). Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Mature T cells can be activated, i.e., by an antigen or other stimulus, to produce, for example, cytokines, biochemical signaling molecules, or receptors that further influence the fate of the T cell population.

B cells can be activated via receptors on their cell surface including the B cell antigen receptor and other accessory molecules to perform accessory cell functions, such as production of cytokines and secretion of Antigen-specific immunoglobulin.

Natural killer (NK) cells have a common progenitor cell with T cells and B cells, and play a role in immune surveillance. NK cells, which comprise up to 15% of blood lymphocytes, do not express antigen specific receptors like B cells, but require the lack of self-MHC for target cell lysis. NK cells are involved in the recognition and killing of certain tumor cells and virally infected cells. In vivo, NK cells are believed to require activation, however, in vitro, NK cells have been shown to kill some types of tumor cells without activation.

The immune system is the body's primary defense against diseases caused by pathogens, namely bacteria, viruses, fungi etc, as well as against diseases caused by abnormal growth of the body's own cells and tissues (i.e. cancerous tumors). Normally, the immune system is able to distinguish between the body's normal cells or "self" and foreign pathogens or abnormal cells or "non-self". The processes by which the immune system refrains from reacting to one's own body is called tolerance. Sometimes, the immune system loses the ability to recognize "self" as normal and the subsequent response directed against the tissue or cells, results in loss of tolerance, a state of autoimmunity. The pathologies resulting from autoimmunity often have serious clinical consequences and are one of the major health problems in the world, especially in developed nations.

One example of such an autoimmune disorder is multiple sclerosis (MS), a progressive disease of the central nervous system (CNS). In MS patients, the patient's own immune system destroys myelin, the protective layer that surrounds and insulates the nerve fibers in the brain and spinal cord. The destruction of the myelin sheath leads to disruption of neurotransmission and scarring damage to the nerve fibers. The end result is the manifestation of numerous symptoms in the affected patient including tingling or numbness, slurred speech, impaired vision, vertigo etc. Over the course of the disease, there is loss of strength in the extremities, leading to problems with movement and in the most severe cases, leading to paralysis of the limbs. Based on clinical diagnosis, there are currently four types of MS classifications, based on which part of the brain or spinal cord are affected, severity, frequency of attacks etc.

Current therapies for MS include corticosteroid drugs (to alleviate symptoms of acute episodes), as well as other drugs like IFN-β and Novantrone®. Novantrone® has been approved for late stage MS patients, specifically for whom other therapies have not worked. Novantrone® is cytotoxic to most cells and therefore as one would expect, has an array of side effects and is toxic at doses required for the maximal therapeutic effects. IFN-β is also toxic, limiting dosage of the drug in MS patients. Furthermore, continuous use of these drugs has been shown to desensitize patients to further use of the same drug, thereby limiting the ability to use these drugs as long term therapeutics. The present invention provides methods of treatment for autoimmune diseases by administering IL-21. Patients with autoimmune disease, such as MS, will particularly benefit from treatment with IL-21 because IL-21 does not have toxic side effects associated with currently-used therapies. These and other uses should be apparent to those skilled in the art from the teachings herein.

SUMMARY OF THE INVENTION

Within one aspect, the present invention provides a method of treating an autoimmune disease comprising administering to a subject in need thereof a therapeutically effective amount of a polypeptide having a functional activity of IL-21.

In one embodiment, the IL-21 polypeptide comprises the sequence of amino acid residues shown in SEQ ID NO:2 from residue 30 to residue 162.

In another aspect, the present invention provides a method of treating autoimmune disease comprising administering to subject a therapeutically effective amount of a polypeptide having a functional activity of IL-21, wherein the autoimmune disease is selected from the group consisting of multiple sclerosis, rheumatoid arthritis, systemic lupus erythematosus, psoriasis, ankylosing spondilitis, scleroderma, Type I diabetes, psoriatic arthritis, osteoarthritis, inflammatory bowel disease, atopic dermatitis and asthma. In one embodiment, the IL-21 polypeptide comprises the sequence of amino acid residues shown in SEQ ID NO:2 from residue 30 to residue 162.

In another aspect, the present invention provides a method of decreasing an autoimmune response in a mammal by administering IL-21 polypeptides. In certain embodiments, the decreased response can be measured as delayed onset of disease or reduction in severity of disease. In any aspects of the invention, the mammal can be a human.

DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to 10 denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "cancer" or "cancer cell" is used herein to denote a tissue or cell found in a neoplasm which possesses characteristics which differentiate: it from normal tissue or tissue cells. Among such characteristics include but are not limited to: degree of anaplasia, irregularity in shape, indistinctness of cell outline, nuclear size, changes in structure of nucleus or cytoplasm, other phenotypic changes, presence of cellular proteins indicative of a cancerous or pre-cancerous state, increased number of mitoses, and ability to metastasize. Words pertaining to "cancer" include carcinoma, sarcoma, tumor, epithelioma, leukemia, lymphoma, polyp, and scirrus, transformation, neoplasm, and the like.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anticomplement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "level" when referring to immune cells, such as NK cells, T cells, in particular cytotoxic T cells, B cells and the like, an increased level is either increased number of cells or enhanced activity of cell function.

The term "level" when referring to viral infections refers to a change in the level of viral infection and includes, but is not limited to, a change in the level of CTLs or NK cells (as described above), a decrease in viral load, an increase antiviral antibody titer, decrease in serological levels of alanine aminotransferase, or improvement as determined by histological examination of a target tissue or organ. Determination of whether these changes in level are significant differences or changes is well within the skill of one in the art.

The term "neoplastic", when referring to cells, indicates cells undergoing new and abnormal proliferation, particularly in a tissue where in the proliferation is uncontrolled and progressive, resulting in a neoplasm. The neoplastic cells can be either malignant, i.e. invasive and metastatic, or benign.

The term "operably linked", when referring to DNA segments, indicates that the segments are arranged so that they function in concert for their intended purposes, e.g., transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery that administration of IL-21 results in inhibiting certain immune cell responses in vitro and in vivo. IL-21 treated dendritic cells are poor antigen presenting cells in vitro. (Brandt K et. al., *Blood*, 102 (12):4090-8, 2003). Furthermore, IL-21 inhibits a delayed type hypersensitivity (DTH) response at the challenge phase, but not the sensitization phase, suggesting that IL-21 does not inhibit priming of antigen-specific T cells but can inhibit an ongoing immune response. IL-21 is also used to inhibit in an experimental allergic encephalomyelitis (EAE), a mouse model for human MS. In the examples that follow, animal models and in vitro assays establish a role for IL-21 in inhibition of autoimmunity by demonstrating the activity of IL-21 on biological samples.

A. Description of IL-21 and its Receptor.

Human IL-21 (SEQ ID NO:1 and SEQ ID NO:2) was designated IL-21, and is described in commonly-owned U.S. Pat. Nos. 6,307,024, and 6,686,178, which is incorporated herein by reference. The IL-21 receptor, (previously designated zalpha11) now designated IL-21R (SEQ ID NO:9 and SEQ ID NO:10), and heterodimeric receptor IL-21R/IL-2Rγ are described in commonly-owned WIPO Publications WO 0/17235, WO 01/77171 and U.S. Pat. No. 6,692,924, which are incorporated herein by reference. As described in these publications, IL-21 was isolated from a cDNA library generated from activated human peripheral blood mononuclear cells (hPBMCs), which were selected for CD3. CD3 is a cell surface marker unique to cells of lymphoid origin, particularly T cells.

The amino acid sequence for the IL-21R indicated that the encoded receptor belonged to the Class I cytokine receptor subfamily that includes, but is not limited to, the receptors for IL-2, IL-4, IL-7, IL-15, EPO, TPO, GM-CSF and G-CSF (for a review see, Cosman, "The Hematopoietin Receptor Superfamily" in *Cytokine* 5(2): 95-106, 1993). The tissue distribution of the receptor suggests that a target for IL-21 is hematopoietic lineage cells, in particular lymphoid progenitor cells and lymphoid cells. Other known four-helical-bundle cytokines that act on lymphoid cells include IL-2, IL-4, IL-7, and IL-15. For a review of four-helical-bundle cytokines, see, Nicola et al., *Advances in Protein Chemistry* 52:1-65, 1999 and Kelso, A., *Immunol. Cell Biol.* 76:300-317, 1998.

For IL-21, the secretory signal sequence is comprised of amino acid residues 1 (Met) to 29 (Ser), and the mature polypeptide is comprised of amino acid residues 30 (Gln) to 162 (Ser) (as shown in SEQ ID NO: 2). In general, cytokines are predicted to have a four-alpha helix structure, with helices A, C and D being most important in ligand-receptor interactions, and are more highly conserved among members of the family. Referring to the human IL-21 amino acid sequence shown in SEQ ID NO:2, an alignment of human IL-21, human IL-15, human IL-4, and human GM-CSF amino acid sequences predicted that IL-21 helix A is defined by amino acid residues 41-56; helix B by amino acid residues 69-84; helix C by amino acid residues 92-105; and helix D by amino acid residues 135-148; as shown in SEQ ID NO: 2. Structural analysis suggests that the A/B loop is long, the B/C loop is short and the C/D loop is parallel long. This loop structure results in an up-up-down-down helical organization. The cysteine residues are absolutely conserved between IL-21 and IL-15. The cysteine residues that are conserved between IL-15 and IL-21 correspond to amino acid residues 71, 78, 122 and 125 of SEQ ID NO: 2. Conservation of some of the cysteine residues is also found in IL-2, IL-4, GM-CSF and IL-21 corresponding to amino acid residues 78 and 125 of SEQ ID NO: 2. Consistent cysteine placement is further confirmation of the four-helical-bundle structure. Also highly conserved in the family comprising IL-15, IL-2, IL-4, GM-CSF and IL-21 is the Glu-Phe-Leu sequence as shown in SEQ ID NO: 2 at residues 136-138. Further analysis of IL-21 based on multiple alignments predicts that amino acid residues 44, 47 and 135 (as shown in SEQ ID NO: 2) play an important role in IL-21 binding to its cognate receptor. Moreover, the predicted amino acid sequence of murine IL-21 (SEQ ID NO:4) shows 57% identity to the predicted human protein. Based on comparison between sequences of human and murine IL-21 well-conserved residues were found in the regions predicted to encode alpha helices A and D.

The corresponding polynucleotides encoding the IL-21 polypeptide regions, domains, motifs, residues and sequences described herein are as shown in SEQ ID NO:1. The amino acid residues comprising helices A, B, C, and D, and loops A/B, B/C and C/D for IL-21, IL-2, IL-4, IL-15 and GM-CSF are shown in Table 1.

scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated IL-21 polypeptides that have a substantially similar sequence identity to the polypeptides of SEQ ID NO:2, or their orthologs. The term "substantially similar sequence identity" is used herein to denote polypeptides comprising at least 70%, at least 80%, at least 90%, at least 95%, or greater than 95% sequence identity to the sequences shown in SEQ ID NO:2, or their orthologs. The present invention also includes polypeptides that comprise an amino acid sequence having at least 70%, at least 80%, at least 90%, at least 95% or greater than 95% sequence identity to the sequence of amino acid residues 1 to 162 or 33 to 162 of SEQ ID NO:2. The present invention further includes nucleic acid molecules that encode such polypeptides. Methods for determining percent identity are described below.

Percent sequence identity is determined by conventional methods. See, for example, Altschul et al., *Bull. Math. Bio.* 48:603 (1986), and Henikoff and Henikoff, *Proc. Natl. Acad.*

TABLE 1

|  | Helix A | A/B Loop | Helix B | B/C Loop | Helix C | C/D Loop | Helix D |  |
|---|---|---|---|---|---|---|---|---|
| IL-21 residues | 41-56 | 57-68 | 69-84 | 85-91 | 92-105 | 106-134 | 135-148 | SEQ ID NO: 2 |
| IL-2 residues | 36-46 | 47-52 | 53-75 | 76-86 | 87-99 | 100-102 | 103-121 | SEQ ID NO: 5 |
| IL-4 residues | 29-43 | 44-64 | 65-83 | 84-94 | 95-118 | 119-133 | 134-151 | SEQ ID NO: 6 |
| IL-15 residues | 45-68 | 69-83 | 84-101 | 102-106 | 107-119 | 120-133 | 134-160 | SEQ ID NO: 7 |
| GM-CSF residues | 30-44 | 45-71 | 72-81 | 82-90 | 91-102 | 103-119 | 120-131 | SEQ ID NO: 8 |

Those skilled in the art will recognize that the sequence disclosed in SEQ ID NO:1 represents a single allele of human IL-21 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the IL-21 polypeptide, are included within the

*Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 2 (amino acids are indicated by the standard one-letter codes).

$$\frac{\text{Total number of identical matches}}{[\text{length of the longer sequence plus the number of gaps introduced into the longer sequence in order to align the two sequences}]} \times 100$$

TABLE 2

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant IL-21. The FASTA algorithm is described by Pearson and Lipman, Proc. Nat'l Acad. Sci. USA 85:2444 (1988), and by Pearson, Meth. Enzymol. 183:63 (1990).

Variant IL-21 polypeptides or polypeptides with substantially similar sequence identity are characterized as having one or more amino acid substitutions, deletions or additions. These changes are preferably of aminor nature, that is conservative amino acid substitutions (see Table 3) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from about 108 to 216 amino acid residues that comprise a sequence that is at least 80%, preferably at least 90%, and more preferably 95%, 96%, 97%, 98%, 99% or more identical to the corresponding region of SEQ ID NO:2. Polypeptides comprising affinity tags can further comprise a proteolytic cleavage site between the IL-21 polypeptide and the affinity tag. Preferred such sites include thrombin cleavage sites and factor Xa cleavage sites.

TABLE 3

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |

TABLE 3-continued

Conservative amino acid substitutions

| | |
|---|---|
| Small: | glycine |
| | alanine |
| | serine |
| | threonine |
| | methionine |

Determination of amino acid residues that comprise regions or domains that are critical to maintaining structural integrity can be determined. Within these regions one can determine specific residues that will be more or less tolerant of change and maintain the overall tertiary structure of the molecule. Methods for analyzing sequence structure include, but are not limited to alignment of multiple sequences with high amino acid or nucleotide identity, secondary structure propensities, binary patterns, complementary packing and buried polar interactions (Barton, Current Opin. Struct. Biol. 5:372-376, 1995 and Cordes et al., Current Opin. Struct. Biol. 6:3-10, 1996). In general, when designing modifications to molecules or identifying specific fragments determination of structure will be accompanied by evaluating activity of modified molecules.

Amino acid sequence changes are made in IL-21 polypeptides so as to minimize disruption of higher order structure essential to biological activity. For example, where the IL-21 polypeptide comprises one or more helices, changes in amino acid residues will be made so as not to disrupt the helix geometry and other components of the molecule where changes in conformation abate some critical function, for example, binding of the molecule to its binding partners, e.g., A and D helices, residues 44, 47 and 135 of SEQ ID NO: 2. The effects of amino acid sequence changes can be predicted by, for example, computer modeling as disclosed above or determined by analysis of crystal structure (see, e.g., Lapthorn et al., Nat. Struct. Biol. 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same cysteine pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structurally similarities between proteins and polypeptides (Schaanan et al., *Science* 257:961-964, 1992).

A Hopp/Woods hydrophilicity profile of the IL-21 protein sequence as shown in SEQ ID NO:2 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in IL-21, hydrophilic regions include amino acid residues 114-119 of SEQ ID NO: 2, amino acid residues 101-105 of SEQ ID NO: 2, amino acid residues 126-131 of SEQ ID NO: 2, amino acid residues 113-118 of SEQ ID NO: 2, and amino acid residues 158-162 of SEQ ID NO: 2.

Those skilled in the art will recognize that hydrophilicity or hydrophobicity will be taken into account when designing modifications in the amino acid sequence of a IL-21 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include residues 100 and 103 as shown in SEQ ID NO: 2. Cysteine residues at positions 71, 78, 122 and 125 of SEQ ID NO: 2, will be relatively intolerant of substitution.

The identities of essential amino acids can also be inferred from analysis of sequence similarity between IL-15, IL-2, IL-4 and GM-CSF with IL-21. Using methods such as "FASTA" analysis described previously, regions of high similarity are identified within a family of proteins and used to analyze amino acid sequence for conserved regions. An alternative approach to identifying a variant IL-21 polynucleotide on the basis of structure is to determine whether a nucleic acid molecule encoding a potential variant IL-21 gene can hybridize to a nucleic acid molecule having the nucleotide sequence of SEQ ID NO:1, as discussed above.

Other methods of identifying essential amino acids in the polypeptides of the present invention are procedures known in the art, such as site-directed mutagenesis or alanine-scanning mutagenesis (Cunningham and Wells, *Science* 244: 1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological or biochemical activity as disclosed below to identify amino acid residues that are critical to the activity of the molecule. See also, Hilton et al., *J. Biol. Chem.* 271:4699 (1996).

The present invention also includes administration of molecules having the functional activity of IL-21. Thus, administration of functional fragments and functional modified polypeptides of IL-21 polypeptides and nucleic acid molecules encoding such functional fragments and modified polypeptides. A "functional" IL-21 or fragment thereof as defined herein is characterized by its proliferative or differentiating activity, by its ability to induce or inhibit specialized cell functions, in particular for immune effector cells, such as NK cells, T cells, B cells and dendritic cells. Functional IL-21 also includes the ability to exhibit anti-cancer and anti-viral effects in vitro or in vivo, or by its ability to bind specifically to an anti-IL-21 antibody or IL-21 receptor (either soluble or immobilized). As previously described herein, IL-21 is characterized by a four-helical-bundle structure comprising helix A (amino acid residues 41-56), helix B (amino acid residues 69-84), helix C (amino acid residues 92-105) and helix D (amino acid residues 135-148), as shown in SEQ ID NO: 2. Thus, the present invention further provides fusion proteins encompassing: (a) polypeptide molecules comprising one or more of the helices described above; and (b) functional fragments comprising one or more of these helices. The other polypeptide portion of the fusion protein can be contributed by another four-helical-bundle cytokine, such as IL-15, IL-2, IL-4 and GM-CSF, or by a non-native and/or an unrelated secretory signal peptide that facilitates secretion of the fusion protein.

Routine deletion analyses of nucleic acid molecules can be performed to obtain functional fragments of a nucleic acid molecule that encodes a IL-21 polypeptide. As an illustration, DNA molecules having the nucleotide sequence of SEQ ID NO:1 or fragments thereof, can be digested with Bal31 nuclease to obtain a series of nested deletions. These DNA fragments are then inserted into expression vectors in proper reading frame, and the expressed polypeptides are isolated and tested for IL-21 activity, or for the ability to bind anti-IL-21 antibodies or zalpha11 receptor. One alternative to exonuclease digestion is to use oligonucleotide-directed mutagenesis to introduce deletions or stop codons to specify production of a desired IL-21 fragment. Alternatively, particular fragments of a IL-21 gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation* 1 Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241: 53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204), and region-directed mutagenesis (Derbyshire et al., *Gene* 46:145 (1986), and Ner et al., *DNA* 7:127, (1988)).

Variants of the disclosed IL-21 nucleotide and polypeptide sequences can also be generated through DNA shuffling as disclosed by Stemmer, *Nature* 370:389 (1994), Stemmer, *Proc. Natl. Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-IL-21 antibodies or soluble zalpha11 receptor, can be recovered from the host cells and rapidly sequenced using modern equipment. These methods allow the rapid determination of the importance of individual amino acid residues in a polypeptide of interest, and can be applied to polypeptides of unknown structure.

In addition, the proteins of the present invention (or polypeptide fragments thereof) can be joined to other bioactive molecules, particularly other cytokines, to provide multi-functional molecules. For example, one or more helices from IL-21 can be joined to other cytokines to enhance their biological properties or efficiency of production.

The present invention thus provides a series of novel, hybrid molecules in which a segment comprising one or more of the helices of IL-21 is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993). It can advantageous to stabilize IL-21 to extend the half-life of the molecule, particularly for extending metabolic persistence in an active state. To achieve extended half-life, IL-21 molecules can be chemically modified using methods described herein. PEGylation is one method commonly used that has been demonstrated to increase plasma half-life, increased solubility, and decreased antigenicity and immunogenicity (Nucci et al., *Advanced Drug Delivery Reviews* 6:133-155, 1991 and Lu et al., *Int. J. Peptide Protein Res.* 43:127-138, 1994).

A limited number of non-conservative amino acids, amino acids that are not encoded by the genetic code, non-naturally occurring amino acids, and unnatural amino acids can substituted for IL-21 amino acid residues.

The present invention also provides polypeptide fragments or peptides comprising an epitope-bearing portion of a IL-21 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)). One of skill in the art would recognize that antigenic, epitope-bearing polypeptides contain a sequence of at least 6, preferably at least 0.9, and more preferably at least 15 to about 30 contiguous amino acid residues of a IL-21 polypeptide (e.g., SEQ ID NO:2). Polypeptides comprising a larger portion of a IL-21 polypeptide, i.e., from 30 to 100 residues up to the entire length of the amino acid sequence are included. Thus, compositions can comprise polypeptides including the IL-21 polypeptide encoded by SEQ ID NO:2 from amino acid number 32 to amino acid number 162, or a contiguous 9 to 131 amino acid fragment thereof.

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219: 660 (1983)). Accordingly, antigenic epitope-bearing peptides and polypeptides of the present invention are useful to raise antibodies that bind with the polypeptides described herein. Hopp/Woods hydrophilicity profiles can be used to determine regions that have the most antigenic potential (Hopp et al., 1981, ibid. and Hopp, 1986, ibid.). In IL-21 these regions include: amino acid residues 114-119, 101-105, 126-131, 113-118, and 158-162 of SEQ ID NO: 2.

Antigenic epitope-bearing peptides and polypeptides preferably contain at least four to ten amino acids, at least ten to fourteen amino acids, or about fourteen to about thirty amino acids of SEQ ID NO:2 or SEQ ID NO:4. Such epitope-bearing peptides and polypeptides can be produced by fragmenting a IL-21 polypeptide, or by chemical peptide synthesis, as described herein. Moreover, epitopes can be selected by phage display of random peptide libraries (see, for example, Lane and Stephen, *Curr. Opin. Immunol.* 5:268 (1993); and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992); Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

Regardless of the particular nucleotide sequence of a variant IL-21 polynucleotide, the polynucleotide encodes a polypeptide that is characterized by its proliferative or differentiating activity, its ability to induce or inhibit specialized cell functions, or by the ability to bind specifically to an anti-IL-21 antibody or zalpha11 receptor. More specifically, variant IL-21 polynucleotides will encode polypeptides which exhibit at least 50% and preferably, greater than 70%, 80% or 90%, of the activity of the polypeptide as shown in SEQ ID NO: 2.

For any IL-21 polypeptide, including variants and fusion proteins, one of ordinary skill in the art can readily generate a fully degenerate polynucleotide sequence encoding that variant using the genetic code and methods known in the art.

The present invention further provides a variety of other polypeptide fusions (and related multimeric proteins comprising one or more polypeptide fusions). For example, a IL-21 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-IL-21 polypeptide fusions can be expressed in genetically engineered cells (to produce a variety of multimeric IL-21 analogs). Auxiliary domains can be fused to IL-21 polypeptides to target them to specific cells, tissues, or macromolecules. For example, a IL-21 polypeptide or protein could be targeted to a predetermined cell type by fusing a IL-21 polypeptide to a ligand that specifically binds to a receptor on the surface of that target cell. In this way, polypeptides and proteins can be targeted for therapeutic or diagnostic purposes. A IL-21 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

Using the methods discussed herein, one of ordinary skill in the art can identify and/or prepare a variety of polypeptides that have substantially similar sequence identity to residues 1-162 or 33-162 of SEQ ID NO: 2, or functional fragments and fusions thereof, wherein such polypeptides or fragments or fusions retain the properties of the wild-type protein such as the ability to stimulate proliferation, differentiation, induce specialized cell function or bind the IL-21 receptor or IL-21 antibodies.

The IL-21 polypeptides used in the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a IL-21 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a IL-21 polypeptide into the secretory pathway of a host cell, a secretory signal sequence (also known as a leader sequence, prepro sequence or pre sequence) is provided in the expression vector. The secretory signal sequence may be that of IL-21, or may be derived from another secreted protein (e.g., t-PA) or synthesized de novo. The secretory signal sequence is operably linked to the IL-21 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980-90, 1989; Wang and Finer, *Nature Med.* 2:714-6, 1996).

A wide variety of suitable recombinant host cells includes, but is not limited to, gram-negative prokaryotic host organisms. Suitable strains of *E. coli* include W3110, K12-derived strains MM294, TG-1, JM-107, BL21, and UT5600. Other suitable strains include: BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, ER1647, *E. coli* K12, *E. coli* K12 RV308, *E. coli* K12 C600, *E. coli* HB101, *E. coli* K12 C600 R.sub.k-M.sub.k-, *E. coli* K12 RR1 (see, for example, Brown (ed.), *Molecular Biology Labfax* (Academic Press 1991)). Other gram-negative prokaryotic hosts can include *Serratia, Pseudomonas, Caulobacter*. Prokaryotic hosts can include gram-positive organisms such as *Bacillus*, for example, *B. subtilis* and *B. thuringienesis*, and *B. thuringienesis* var. *israelensis*, as well as *Streptomyces*, for example, *S. lividans, S. ambofaciens, S. fradiae*, and *S. griseofuscus*. Suitable strains of *Bacillus subtilus* include BR151, YB886, MI119, MI120, and B170 (see, for example, Hardy, "*Bacillus* Cloning Methods," in *DNA Cloning: A Practical Approach*, Glover (ed.) (IRL Press 1985)). Standard techniques for propagating vectors in prokaryotic hosts are well-known to those of skill in the art (see, for example, Ausubel et al. (eds.), *Short Protocols in Molecular Biology*, $3^{rd}$ Edition (John Wiley & Sons 1995); Wu et al., *Methods in Gene Biotechnology* (CRC Press, Inc. 1997)). In one embodiment, the methods of the present invention use IL-21 expressed in the W3110 strain, which has been deposited at the American Type Culture Collection (ATCC) as ATCC # 27325.

When large scale production of IL-21 using the expression system of the present invention is required, batch fermentation can be used. Generally, batch fermentation comprises that a first stage seed flask is prepared by growing *E. coli* strains expressing IL-21 in a suitable medium in shake flask culture to allow for growth to an optical density (OD) of between 5 and 20 at 600 nm. A suitable medium would contain nitrogen from a source(s) such as ammonium sulfate, ammonium phosphate, ammonium chloride, yeast extract, hydrolyzed animal proteins, hydrolyzed plant proteins or hydrolyzed caseins. Phosphate will be supplied from potassium phosphate, ammonium phosphate, phosphoric acid or sodium phosphate. Other components would be magnesium chloride or magnesium sulfate, ferrous sulfate or ferrous chloride, and other trace elements. Growth medium can be supplemented with carbohydrates, such as fructose, glucose, galactose, lactose, and glycerol, to improve growth. Alternatively, a fed batch culture is used to generate a high yield of IL-21 protein. The IL-21 producing *E. coli* strains are grown under conditions similar to those described for the first stage vessel used to inoculate a batch fermentation.

Following fermentation the cells are harvested by centrifugation, re-suspended in homogenization buffer and homogenized, for example, in an APV-Gaulin homogenizer (Invensys APV, Tonawanda, N.Y.) or other type of cell disruption equipment, such as bead mills or sonicators. Alternatively, the cells are taken directly from the fermentor and homogenized in an APV-Gaulin homogenizer. The washed inclusion body prep can be solubilized using guanidine hydrochloride (5-8 M) or urea (7-8 M) containing a reducing agent such as beta mercaptoethanol (10-100 mM) or dithiothreitol (5-50 mM). The solutions can be prepared in Tris, phopshate, HEPES or other appropriate buffers. Inclusion bodies can also be solubilized with urea (2-4 M) containing sodium lauryl sulfate (0.1-2%). In the process for recovering purified IL-21 from transformed *E. coli* host strains in which the IL-21 is accumulates as refractile inclusion bodies, the cells are disrupted and the inclusion bodies are recovered by centrifugation. The inclusion bodies are then solubilized and denatured in 6 M guanidine hydrochloride containing a reducing agent. The reduced IL-21 is then oxidized in a controlled renaturation step. Refolded IL-21 can be passed through a filter for clarification and removal of insoluble protein. After the IL-21 protein is refolded and concentrated, the refolded IL-21 protein is captured in dilute buffer on a cation exchange column and purified using hydrophobic interaction chromatography.

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

A variety of assays known to those skilled in the art can be utilized to detect antibodies which bind to IL-21 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant IL-21 protein or polypeptide.

The methods of the present invention also contemplate using chemically modified IL-21 compositions, in which a IL-21 polypeptide is linked with a polymer. Illustrative IL-21 polypeptides are soluble polypeptides that lack a functional transmembrane domain, such as a mature IL-21 polypeptide. Typically, the polymer is water soluble so that the IL-21 conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce IL-21 conjugates.

IL-21 conjugates used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A IL-21 conjugate can also comprise a mixture of such water-soluble polymers.

B. The Use of IL-21 for Treating Autoimmune Diseases

IL-21 was isolated from tissue known to have important immunological function and which contain cells that play a role in the immune system. IL-21 is expressed by CD3+ selected, activated peripheral blood cells, and it has been shown that IL-21 expression increases after T cell activation.

Experiments have demonstrated that IL-21 polypeptides have an effect on the growth/expansion and/or differentiated state of NK cells or NK progenitors. (Toomey J A et al., *J. Leukoc. Biol.*, 74:233-242, 2003; Strengell M et al., *J. Immunol.* 170:5464-5469, 2003; Parrish-Novak J et. al., *Nature*, 408:57-63, 2000) A composition comprising IL-21 and IL-15 has been shown to stimulate NK progenitors and NK cells, and was more potent than previously described factors and combinations of factors. (Toomey J A et al., supra, 2003; Strengell M supra, 2003) Moreover, IL-21 promoted NK-cell expansion, and IL-21 largely overcame the inhibitory effects of IL-4 on NK-cell growth, synergized with IL-2 to promote NK cell growth, and selectively promoted the expression of IFN-γ and depressed IL-13 expression. (Toomey J A et al., J. Leukoc. Biol. supra, 2003; Strengell M et al., supra, 2003: Parrish-Novak et. al., supra, 2002).

Dendritic cells are a subclass of antigen presenting cells (APCs) critical in the initiation and regulation of adaptive immunity against pathogens and tumors, as well as triggering autoimmunity (reviewed in Guermonprez P et al., *Ann. Rev. Immunol.*, 20:621-667, 2002; Heath W R and Carbone F R, *Ann. Rev. Immunol.*, 19:47-64, 2001). As the main source of cells presenting antigen to T cells, it is more clear that DCs play an important role in establishing and maintaining tolerance and avoiding autoimmunity. DCs have been shown to confer tolerance to self antigens in the thymus and periphery. Furthermore, DCs can be generated in vitro and in vivo that can specifically induce tolerance in mice and inhibit autoimmunity in vivo (Wakkach A et al., *Immunity* 18:605-617, 2003: Sato K et al., *Immunity* 18:367-379, 2003). These results suggest that regulation of DC function is crucial in modulating the immune response in vivo and shifting the balance from autoimmunity to tolerance of self antigens (Mehling A and Beissert S, *Crit. Rev. Biochem. Mol. Biol.*, 38:1-21, 2003: Steinman R M et al., *Ann. N Y Acad. Sci.*, 987:15-25, 2003: Steinman R M et al., *Ann. Rev. Immunol.*, 21:685-711, 2003). Cytokines can act as modulators of dendritic cell function and thereby inhibit autoimmunity. The present invention provides methods for decreasing an autoimmune response in a mammal by administering a composition of IL-21. The present invention also provides methods of treating autoimmune diseases such as multiple sclerosis, rheumatoid arthritis, systemic lupus erythematosus, psoriasis, ankylosing spondilitis, scleroderma, Type I diabetes, psoriatic arthritis, osteoarthritis, inflammatory bowel disease, atopic dermatitis and asthma by administering an IL-21 composition to afflicted mammals, in particular humans. The treatment with IL-21 results in some beneficial effect to the subject and may be measured in a variety of ways. Specific measurements may be demonstrate that administration of IL-21 results in the delay of onset of the specific autoimmune disease or reduction in the severity of the disease. The parameters used to demonstrate a beneficial effect to the subject will depend upon the disease diagnosis, the patient's underlying health, but could reduce the disease's severity, complications, such as side effects caused by toxicity, cost, and or provide a more convenient treatment regime. Treatment could result in decreased damage to organs such as liver, lungs, heart, central nervous system, and gastrointestinal system. It is well within the skill of a clinician to determine what will determine a therapeutic benefit to a patient.

1. IL-21 Treated Dendritic Cells Inhibit Proliferation of Antigen-Specific CD4 T Cells In Vitro In the present invention, the ability of IL-21 to inhibit immune responses is evaluated by culturing dendritic cells (DCs) with IL-21 and using the cultured DCs as antigen-presenting cells (APCs). DCs are generated from BALB/c (H-$2^d$) mouse bone marrow by extracting bone marrow cells and culturing the cells with granulocyte-macrophage colony stimulating factor (GM-CSF) or with GM-CSF+IL-21 or GM-CSF+IL-15 for 10 days. The DCs are then washed and incubated with an antigen, such as a peptide of chicken ovalbumin (OVA323-334). The antigen-pulsed DCs are washed and then cultured with varying concentrations of CD4$^+$ T cells from DO11.10 transgenic mice. All CD4$^+$ T cells from DO11.10 transgenic mice express a transgenic T cell receptor (TCR) that is specific for the OVA323-334 peptide in the context of the I-A$^d$. CD4$^+$ T cells that come in contact with DCs pulsed with OVA323-334 peptide become activated and proliferate. Proliferation can be measured by incorporation of $^3$H thymidine in the dividing cells. DO11.10 T cells co-cultured with DCs cultured in GM-CSF or GM-CSF+IL-15 proliferate rapidly and show increased incorporation of $^3$H-thymidine. In contrast, DO11.10 T cells co-cultured with DCs derived in GM-CSF+IL-21 proliferate poorly as indicated by the lower incorporation of $^3$H-thymidine. Thus, DCs exposed to GM-CSF plus IL-21 are poor antigen presenting cells in vitro.

Dendritic cells may also be derived from mouse bone marrow by culturing with flt3L. DCs derived by culturing with flt3L+IL-21 are also poor antigen presenting cells compared to DCs derived by culturing with flt3L alone. Therefore, addition of IL-21 to dendritic cell cultures prevents the development of effective APC capable of stimulating cognate T cells to proliferate.

2. IL-21 Derived Dendritic Cells are Poor Antigen Presenting Cells In Vivo

In the present invention, it is demonstrated that DCs derived from bone marrow cells in the presence of IL-21 are poor antigen presenting cells. DCs cultured with GM-CSF or GM-CSF+IL-21 for 10 days are pulsed with fluorescein isothiocyanate (FITC), washed and then injected into the footpads of mice. Six days later, the thickness of mice ears is measured. FITC-DC immunized mice are challenged in the left ear by injecting with control PBS and in the right ear by injecting with FITC in PBS. The ear thickness is measured 24 hours later. Mice immunized with DCs derived from cultures in GM-CSF (+FITC) show an increased thickening of the ear in 24 hours, a demonstration of an immune response against FITC. In contrast, mice immunized with DCs derived by culturing in GM-CSF+IL-21 (+FITC) do not show an increase in ear thickness suggesting a lack of immune response generated by GM-CSF+IL-21 cultured DCs (Brandt K et. al., *Blood* (in press), 2003) The present invention shows that DCs cultured in IL-21 are poor antigen presenting cells in vivo.

3. Dendritic Cells Cultured in IL-21 Express Lower Levels of MHC Class II and Increased Levels of MHC Class I.

As specified above, DCs are derived from mouse bone marrow and cultured with GM-CSF or GM-CSF+IL-21. DCs are washed and stained with FITC-conjugated antibodies against MHC Class II (I-A$^d$) and PE-conjugated antibodies against MHC Class I (H-2 K$^d$), along with markers for mouse dendritic cells, CD11b and CD11c. DCs cultured with GM-CSF express high levels of MHC Class II and MHC Class I molecules. DCs derived from culturing with GM-CSF+IL-21 express lower levels of MHC Class II molecules and higher levels of MHC Class I molecules compared to DCs cultured with GM-CSF alone. Expression of lower levels of MHC Class II may result in decreased stimulation and proliferation of CD4+ T cells in vitro.

Additional evidence demonstrates that IL-21 affects proliferation and/or differentiation of T cells and B cells in vivo. It is shown that IL-21 can either inhibit or enhance the proliferation of normal B cells depending on the nature of the co-stimulus provided the cells. IL-21 inhibits the proliferation of some B cell lines, but not others, even though most non-responder cell lines express IL-21R as measured by specific IL-21 binding. Many human B cell lines will grow in and kill SCID mice Bonnefoix et al., *Leukemia and Lymphoma* 25:169-178, 1997). Examples herein describe three B-cell lines which are inhibited by IL-21 and three B cell lines which did not respond to IL-21. All of the lymphoma cell lines were IL-21 receptor positive. The lymphoma cells were implanted into SCID mice to determine whether IL-21 could prolong the survival of lymphoma bearing animals. IL-21 exhibited significant efficacy against the three cell lines whose proliferation was inhibited in vitro. In a separate experiment, NK-cell depletion of the SCID mice failed to abrogate the IL-21 effect in the IM-9 model, suggesting that NK-cells are not required for the efficacy of IL-21 in this model. See, co-owned WO03/103589, incorporated herein by reference, for a detailed discussion.

TABLE 4

| Treatment | MHC Class II (MFI) | MHC Class I (MFI) |
| --- | --- | --- |
| GM-CSF (10 days) | 230 | 70 |
| GM-CSF + IL-21 (10 days) | 57 | 121 |
| GM-CSF (10 days) + IL-21 (final 3 days) | 92 | 105 |

4. IL-21 Treatment Inhibits DTH at the Challenge Phase but not at the Sensitization Phase.

DTH responses are classic immune responses that are initiated by CD4+ T cells and mediated by T cells, neutrophils and macrophages. A DTH response is a good indicator of a CD4+ T cell mediated response. In one model used to investigate CD4+ T cell response, mice are immunized subcutaneously with chicken ovalbumin protein (OVA) in either of 2 adjuvants, RIBI or CFA. This phase is called the sensitization phase (days 0-6). Ear measurements are taken seven days later. Mice are then injected in the ear with control PBS (left ear) or OVA (right ear). This phase is called the challenge phase (days 7-8). Immune responses generated to OVA induce inflammation in the ear resulting in an increase in ear thickness in 24 hours. This is measured using calipers. A DTH experiment is done as specified above. (See, e.g., Oura et al., *Blood* 101:560-567, 2003; Zaloom et al., *Immunology* 72:584-587, 1991.) To demonstrate administration of IL-21 results in CD4+ T cell responses, groups of mice are injected intraperitoneally with a single injection/day of PBS or IL-21 from either days 0-6 (sensitization phase) or days 7-8 (challenge phase). Mice treated with IL-21 from days 0-6 show normal immune responses as shown by a similar increase in ear thickness in the OVA-treated ears as in PBS treated mice. In contrast, mice treated with IL-21 from days 7-8 show a decreased thickening of the OVA-treated ear compared to those of PBS treated mice. This demonstrates that IL-21 inhibits DTH at the challenge phase and is able to inhibit an ongoing immune response. This also demonstrates that IL-21 does not inhibit the generation of an immune response because it does not inhibit DTH when admininstered at the sensitization phase.

TABLE 5

| Treatment | Mean Change in ear thickness (PBS) ($\times 10^{-3}$ in) | Mean Change in ear thickness (OVA) ($\times 10^{-3}$ in) | P value (vs PBS treated group) |
| --- | --- | --- | --- |
| PBS (d0-8) | 1.27 ± 0.59 | 7.2 ± 1.12 | — |
| 100 ug IL-21 (d0-6) | 0.91 ± 0.75 | 7.08 ± 2.5 | 0.9162 |
| 100 ug IL-21 (d7-8) | 0.45 ± 1.03 | 2.38 ± 0.76 | <0.0001 |

5. IL-21 Mediated Inhibition of DTH at the Challenge Phase is Dose Dependent

As specified above, a DTH response is tested in a mouse model by treating mice with either PBS or varying doses of IL-21 from days 7-8. The data show increasing doses of IL-21 result in increased inhibition of ear thickness in mice when administered at the challenge phase. This demonstrates that the inhibition of inflammation by IL-21 is dose dependent.

TABLE 6

| Treatment (d7-8) | Mean Change in ear thickness (PBS) ($\times 10^{-3}$ in) | Mean Change in ear thickness (OVA) ($\times 10^{-3}$ in) | P value (vs PBS treated group) |
| --- | --- | --- | --- |
| PBS | 1 + 0.77 | 7.9 ± 1.9 | — |
| 5 ug IL-21 | 0.76 + 0.77 | 6.4 ± 1.45 | 0.1795 |
| 25 ug IL-21 | 0.145 + 0.402 | 4.98 ± 1.42 | 0.0070 |
| 50 ug IL-21 | 0.89 + 0.65 | 4.6 ± 1.2 | 0.0021 |
| 100 ug IL-21 | 1.02 + 0.73 | 4.29 ± 1.2 | 0.0012 |
| 200 ug IL-21 | 0.42 + 0.54 | 3.91 ± 1.75 | 0.0014 |
| 50 ug IL-2 | 0.52 + 0.48 | 7.47 ± 1.47 | 0.6762 |

6. IL-21 Inhibits Paw Scores and Paw Thickness in a Mouse Model for Rheumatoid Arthritis (Collagen-Induced Arthritis Model)

Rheumatoid arthritis is an autoimmune disorder where the immune responses of the body are targeted against the body's own proteins, in particular collagen, a protein that is the foundation of multiple tissues, specifically joints. The resulting immune response against collagen leads to destruction of the joints. Over time, the patient can lose the ability to move their fingers and toes and can experience acute pain in the joints and knees. Serum from arthritis patients have increased amounts of TNFα (tumor necrosis factor) and antibodies against collagen, both of which are not only indicators of chronic disease but also contribute towards the pathology of the disease. (Smolen and Stein+er G, *Nat. Rev. Drug Discov.*, 2:473-488, 2003; Firestein, *Nature* 423:356-361, 2003.) Furthermore, the disease is initiated and mediated by CD4+ T cells. DCs present collagen as an antigen to CD4+ T cells. The collagen-induced arthritis (CIA) model is a mouse model for rheumatoid arthritis that reflects to large extent the disease seen in humans. (Moore, *Methods Mol. Biol.* 225:175-179, 2003: Waksman, *Scand. J. Immunol.*, 56:12-34, 2002). Mice are immunized with 2 doses of collagen emulsified in CFA at the base of the tail. This results in swelling of the paws that increases over a period of time and can be both visually scored and measured using calipers. Based on data showing that DCs cultured in IL-21 inhibit CD4+ T cell responses, IL-21 is administered to groups of collagen-immunized mice, and effects on disease scores are evaluated. Inhibition of paw scores and thickness by IL-21 is indicative of it's inhibitory effect on an ongoing autoimmune response.

7. IL-21 Treatment Delays Onset of Disease in a Mouse Model for Multiple Sclerosis Experimental allergic encephalomyelitis (EAE) is a mouse model for human MS (*Gold* et al., *Mol. Med. Today,* 6:88-91, 2000; Anderton et al., *Immunol. Rev.,* 169:123-137, 1999). There are multiple ways of inducing disease in mice. One such method is to immunize mice with a peptide of the myelin protein MOG (myelin oligodendrocyte glycoprotein). This protein is present on the outside of the myelin sheath and acts as a protective layer for myelin. Mice are immunized sub-cutaneously with MOG peptide (MOG35-55) emulsified in RIBI adjuvant on day 0. Mice are then injected intravenously with pertussis toxin (PT) on day 2. The mice start showing symptoms of paralysis starting with a limp tail, wobbly motion, followed by hind limb and forelimb paralysis, which are scored according to several different parameters that measure the timing, extent and severity of disease. Delay in onset of disease indicates that the drug is modifying the disease process in mice. Decrease in incidence indicates that the drug is having an effect on the number of mice that are getting sick. Decrease in clinical score indicates that the drug has an effect on the severity of disease. Groups of mice are given PBS or IL-21 on days 1 through 15. The onset of symptoms, incidence of disease scores and severity of disease scores in IL-21 treated mice indicates the effect of IL-21 on these parameters in this model. Mice (n=13/gp) are immunized s.c with 100 µg MOG35-55 in RIBI adjuvant on d0. All mice receive 200 ng pertussis toxin i.v on d2. Groups of mice are treated with PBS, 100 µg BSA, 10 ug or 100 µg IL-21 on d0-20 i.p. As specified above, mice are scored for clinical signs and weight loss daily from d0-d30. Both the 10 µg and 100 µg IL-21 treated mice show a delay in the onset of disease compared to PBS or BSA treated animals. The delay seen in the 100 µg group is larger than in the 10 µg group suggesting that the effect of IL-21 is dose dependent.

TABLE 7

| Treatment groups D0-20 | Mean Day of Onset (MDO) | P value (vs PBS group) |
|---|---|---|
| PBS | 10.3 ± 2.4 | — |
| 100 ug BSA | 10.1 ± 1.9 | 0.7844 |
| 10 ug IL-21 | 12.8 ± 3.3 | 0.0500 |
| 100 ug IL-21 | 14.5 ± 2.6 | 0.0005 |

8. IL-21 Derived Dendritic Cells can Inhibit Autoimmune Responses In Vivo

As specified above, dendritic cells cultured in IL-21 are poor antigen presenting cells in vitro and in vivo as demonstrated by their inability to stimulate proliferation of $CD4^+$ T cells in vitro and their inability to stimulate a response to antigen in vivo. To test if IL-21 derived DCs can be used to inhibit autoimmune disease in vivo, mice are immunized with MOG35-55 peptide in RIBI adjuvant on day 0. Dendritic cells cultured in GM-CSF+IL-21 are pulsed with MOG35-55 peptide and injected into footpads of mice. Mice are injected with pertussis toxin i.v. on day 2. The ability of the IL-21 cultured DCs to inhibit autoimmune disease is indicated by decreased disease scores, delayed onset and decreased incidence of disease in mice.

A. Hypersensitivity

Hypersensitivity is classified by type. Type I hypersensitivity is immediate and IgE related; Type II hypersensitivity is antibody and complement related cytotoxicity; Type III hypersensitivity is antigen-antibody complex mediated; and Type IV hypersensitivity is delayed type hypersensitivity (DTH).

Type IV hypersensitivity responses are mediated by T cells predominantly by Th1 cells and $CD8^+$ T cells, although there is significant involvement of macrophages and neutrophils. There are three well-studied examples of Type IV responses, DTH, contact hypersensitivity (CH), and Celiac Disease (gluten-sensitive enteropathy). Contact hypersensitivity is a response to antigens that are absorbed via the skin, such as metals and poison ivy. There is support for classifying atopic dermatitis (AD) as a form of CH, but the classification is still being debated. IL-21 has been shown to inhibit DTH at the challenge phase (acute and transient) responses and IL-21 stimulated DCs mediate weak DTH and CH responses and therefore, will be useful in the treatment of AD, as well as other disorders associated with CH.

Testing for AD requires primarily transgenic models, however, cells obtained from AD patients can be used as an in vitro system to evaluate the effects of IL-21 on AD. Moreover, evaluation of T cell responses, antigen presenting cell (APC) responses and immunohistochemistry in CH models provide valuable information for treating AD patients with IL-21. (Leung and Bieber, *The Lancet,* 361: 151-160, 2003: Maurer, *Curr. Problems Dermatol.,* 122:38-43, 1995; Akhavan and Cohen, *Clin. Dermatol.,* 21:158-162, 2003; Herrick et al., *J. Immunol.,* 170:2488-2495, 2003; Marsella and Olivry, *Clin. Dermatol.,* 21:122-133, 2003).

B. Inflammatory Bowel Disease

Inflammation in the gut resulting from defective immune regulation, known as inflammatory bowel disease (IBD) is characterized into two broad disease definitions, Crohn's disease (CD) and Ulcerative colitis (UC). Generally, CD is thought to be due to dysfunction in the regulation of Th1 responses, and UC is believed to be due to dysfunction in the regulation of Th2 responses. Multiple cytokines, chemokines, and matrix metaloproteinases have beens shown to be upregulated in inflamed lesions from IBD patients. These include IL-1, IL-12, IL-18, IL-15, TNF-α, IFN-γ, MIP1α, MIP1β, and MIP2. Currently REMICADE® (Centocor, Malvern, Pa.) is the only drug that has successfully been used to target the disease itself when treating CD patients, with other treatments generally improving the quality of life of patients. IL-21 inhibition of the autoimmune response associated with IBD is demonstrated in IBD models, such as the mouse DSS, TNBS, CD4+CD45Rbhi, mdrla−/− and graft v. host disease (GVHD) intestinal inflammation models. (Stadnicki A and Colman R W, Arch Immunol Ther Exp 51:149-155, 2003; Pizarro TT et al., Trends in Mol Med 9:218-222, 2003). One experimental model for human IBD is the oral administration of dextran sodium sulfate (DSS) to rodents. DSS induces both acute and chronic ulcerative colitis with features somewhat resembling histological findings in humans. Colitis induced by DSS involves gut bacteria, macrophages and neutrophils, with a minor role for T and B cells (Mahler et al., *Am. J. Physiol.* 274:G544-G551, 1998; Egger et al., *Digestion* 62:240-248, 2000). TNBS-induced colitis is considered a Th1 mediated disease and therefore resembles CD more than UC in humans. Tri-nitro benzene sulfonic acid (TNBS) is infused into mice intra-rectally in varying doses (strain dependent) to induce antigen specific (TNBS) T cell response that involves secretion of Th1-like cytokines IL-12, IL-18 and IFNγ. Colitis involves recruitment of antigen-specific T cells, macrophages and neutrophils to the site of inflammation (Neurath et al., *Int. Rev. Immunol.,* 19:51-62, 2000; Dohi T et al., *J. Exp.*

*Med.* 189:1169-1179, 1999). Another relatively new model for colitis is the CD4+CD45RB$^{hi}$ transfer model into SCID mice. CD4$^+$ T cells can be divided broadly into 2 categories based on expression of CD45Rb. CD4$^+$ CD45RB$^{hi}$ cells are considered naïve T cells whereas CD4+CD45Rb$^{lo}$ cells are considered regulatory T cells. Transfer of whole CD4$^+$ T cells into syngenic SCID mice does not induce symptoms of colitis. However, if only the CD4+CD45RB$^{hi}$ T cells are injected into SCID mice, mice develop colitis over a period of 3-6 weeks. Co-transfer of the CD4+CD45Rb$^{lo}$ regulatory T cells along with the naïve T cells inhibits colitis suggesting that the regulatory T cells play an important role in regulating the immune response (Leach et al., *Am. J. Pathol.,* 148:1503-1515, 1996; Powrie et al., *J. Exp. Med.,* 179:589-600, 1999). This model will demonstrate that IL-21 inhibits colitis by upregulating T regulatory function via its ability to generate tolerogenic DCs in mice. A clinically relevant model of colitis associated with bone marrow transplantation is GVHD-induced colitis. Graft-versus-host disease (GVHD) develops in immunoincompetent, histocompatible recipients of effector cells, which proliferate and attack host cells. Patients receiving allogeneic bone marrow transplantation or severe aplastic anemia are at risk for GVHD. In both mice and humans, diarrhea is a common and serious symptom of the syndrome. In human, both colonic and small intestinal disease have been observed. Mouse models for GVHD-induced colitis show similar histological disease as seen in humans. These mouse models can therefore be used to assess the efficacy of colitis inhibiting drugs for GVHD (Eigenbrodt et al., *Am. J. Pathol.,* 137:1065-1076, 1990; Thiele et al., *J. Clin. Invest.,* 84:1947-1956, 1989).

C. Systemic Lupus Erythematosus

Systemic lupus erythematosus (SLE) is an immune-complex related disorder characterized by chronic IgG antibody production directed at ubiquitous self antigens (anti-dsDNA). The effects of SLE are systemic, rather than localized to a specific organ. Multiple chromosomal loci have been associated with the disease and may contribute towards different aspects of the disease, such as anti-dsDNA antibodies and glomerulonephritis. CD4$^+$ T cells have been shown to play an active part in mouse models of SLE (Horwitz, *Lupus* 10:319-320, 2001; Yellin and Thienel, *Curr. Rheumatol. Rep.,* 2:24-37, 2000). The role for CD8$^+$ T cells is not clearly defined, but there is evidence to suggest that "suppressor" CD8$^+$ T cell function is impaired in lupus patients (Filaci et al., *J. Immunol.,* 166:6452-6457, 2001; Sakane et al, *J. Immunol.,* 137:3809-3813, 1986).

IL-21 has been shown to modulate antibody responses by directly acting on B cells. (Mehta et al., *J. Immunol.,* 170:4111-4118, 2003; Ozaki et al., *Science,* 298:1630-1634, 2002; Suto et al., *Blood,* 100:4565-4573, 2002). Moreover, because IL-21 enhances CD8 T cell activity, administration of IL-21 would provide a more robust T cell suppressor function in lupus patients where that function is compromised.

Sera from human SLE patients and mouse models are assayed for IL-21 activity. CD8$^+$ T cell suppressor activity in PBLs from human SLE patients after culture with of IL-21 is evaluated in vitro. Suppressor activity of CD8$^+$ T cells from SLE patients is evaluated by their ability to inhibit anti-CD3 induced proliferation of autologous PBMC. Inhibition function correlates with secretion of IFNγ and IL-6 in the cultures. Increased IFNγ and IL-6 in cultures from IL-21 treated patients might indicate higher suppressor activity (Filaci et al., *J. Immunol.* 166:6452-6457, 2001)

D. Psoriasis

Psoriasis is a chronic inflammatory skin disease that is associated with hyperplastic epidermal keratinocytes and infiltrating mononuclear cells, including CD4+ memory T cells, neutrophils and macrophages (Christophers, *Int. Arch. Allergy Immunol.,* 110:199, 1996). It is currently believed that environmental antigens play a significant role in initiating and contributing to the pathology of the disease. However, it is the loss of tolrance to self antigens that is thought to mediate the pathology of psoriasis. Dendritic cells and CD4$^+$ T cells are thought to play an important role in antigen presentation and recognition that mediate the immune response leading to the pathology. We have recently developed a model of psoriasis based on the CD4+CD45RB transfer model (Davenport et al., *Internat. Immunopharmacol.,* 2:653-672). IL-21 is administered to mice that are injected with psoriasis inducing cells and the effects on clinical score (skin disease) is evaluated, showing beneficial effects of IL-21.

IL-21 can be administered in combination with other agents already in use in autoimmunity including immune modulators such as interferon α (IFN-α), IFNγ, NOVANTRONE®, ENBREL®, REMICADE®, LEUKINE® and IL-2 Establishing the optimal dose level and scheduling for IL-21 is done by a variety of means, including study of the pharmacokinetics and pharmacodynamics of IL-21; determination of effective doses in animal models, and evaluation of the toxicity of IL-21. Direct pharmacokinetic measurements done in primates and clinical trials can then be used to predict theoretical doses in patients that achieve plasma IL-21 levels that are of sufficient magnitude and duration to achieve a biological response in patients. In addition IL-21 stimulates a variety of responses in normal dendritic cells, such that surrogate markers can be employed to measure the biological activty of IL-21 on effector cells in patients.

An IL-21-saporin fusion toxin, or other IL-21-toxin fusion, can be employed against autoimmune diseases, extending the range of diseases that can be treated with IL-21. Moreover, such IL-21-toxin fusions can be employed against other autoimmune diseases wherein IL-21 binds autoimmune B cells, CD8$^+$ its receptors. Fusion toxin mediated activation of the IL-21 receptor provides two independent means to inhibit the growth of the target cells, the first being identical to the effects seen by the ligand alone, and the second due to delivery of the toxin through receptor internalization. The lymphoid restricted expression pattern of the IL-21 receptor suggests that the ligand-saporin conjugate can be tolerated by patients.

IL-21 is a product of activated CD4$^+$ "helper" T-cells which are required for both humoral and cell-mediated immunity and for sustaining long-term memory to antigenic re-challenge (U.S. Pat. No. 6,307,024; Parrish-Novak et al., *Nature* 408:57-63, 2000). The receptor for IL-21 is expressed on cells that mediate anti-cancer and immune responses and previous experiments have shown that IL-21 can stimulate the proliferation of these cell types in vitro (commonly-owned WIPO Publication No.s WO 0/17235 and WO 01/77171). Inhibition of an immune response can be established in at least 2 phases—during antigen presentation or during an effector response to inhibit an existing response. As specified above, IL-21 can specifically inhibit antigen presentation to CD4$^+$ T cells. A significant number of autoimmune responses are directed through CD4$^+$ T cell activation. In the antigen presentation phase, inhibition of antigen presentation to CD4$^+$ T cells by exposure to IL-21 would sustain an inhibitory immune response, thereby inhibiting autoimmunity. In the effector phase, IL-21 enhances CD8+ and NK cell activity. Although it is generally thought that CD8+ T cells and NK cells contribute towards autoimmunity, several lines of evidence suggest that these cells play regulatory roles during autoimmunity and that depleting CD8+ and/or NK cells enhances severity of an autoimmune response. The enhancement of an autoimmune response has been demonstrated in a mouse model for MS. In this model, depletion of cells expressing perforin (CD8+ and NK cells) exacerbated EAE in mice (Malipiero U et. al., *Eur J. Immunol.* 27:3151-3160, 1997). Furthermore, depletion of NK cells increased disease severity and activation of NK cells protected mice from EAE (Singh AK et al. *J Exp Med.* 194:1801-1811, 2001). These experiments suggest that the ability of IL-21 to enhance CD8+ T cell and NK cell activity will play a role in regulating the autoimmune response by inhibition. Thus, IL-21 can inhibit an ongoing immune response by acting on antigen presenting cells, as well as effector cells, like CD8+ T cells and NK cells.

The invention is further illustrated by the following non-limiting examples.

EXAMPLES

Example 1

Dendritic Cells Cultured with IL-21 are Poor Antigen Presenting Cells In Vitro

Mouse dendritic cells are derived by culturing BALB/c strain bone marrow cells in GM-CSF or GM-CSF+IL-15 or GM-CSF+IL-21. The dendritic cells are phenotyped by flow cytometry to study expression of MHC Class I and MHC Class II molecules. Furthermore, the dendritic cells are pulsed with OVA323-334 peptide and used as antigen presenting cells to DO11.10 transgenic T cells.

Dendritic cells cultured in GM-CSF+IL-21 express lower levels of MHC Class II molecules and higher levels of MHC Class I molecules than DCs cultured with GM-CSF alone. Dendritic cells cultured with GM-CSF alone or GM-CSF+IL-15 induce efficient proliferation of antigen specific DO11.10 T cells in vitro. In contrast, DCs cultured in GM-CSF+IL-21 induce much less proliferation compared to the cultures mentioned above. Similarly, DCs cultured with flt3L alone induce efficient proliferation of transgenic DO11.10 T cells. DCs cultured with flt3L+IL-21 are not good inducers of proliferation.

B. Study Design

Female BALB/c mice, approximately 8-10 weeks of age are euthanized. The femurs from these mice are isolated and crushed using a mortar and pestle to extract marrow cells. Red blood cells are lysed by incubating cells for 2 minutes with ACK lysis buffer (0.15M NH4Cl, 1 mM KHCo3, 0.1 mM EDTA) followed by neutralization with RPMI-10 media (RPMI with 10% FBS). The cells are washed once with RPMI-10 media and cultured at 2 million cells/ml in 24 well plates in complete DMEM media in a total volume of 3 ml/well with the indicated cytokines. Cells are cultured with 20 ng/ml recombinant murine GM-CSF (rmGM-CSF, R & D systems) or rmGM-CSF+30 ng/ml recombinant murine IL-15 (rmIL-15, R & D systems) or rmGM-CSF+30 ng/ml) recombinant murine IL-21 (rmIL-21, Zymogenetics). Cells are re-fed with fresh media and cytokines every 4 days. On day 10 after start of culture, cells are harvested and used for either flow cytometry analysis or APC assay.

For flow cytometry analysis of DCs, the expression of cell surface markers are analyzed by standard 3-color flow cytometry using the Becton Dickinson (BD) FACsCalibur instrument. All antibodies are obtained from BD Pharmingen (San Diego, Calif.). Fluorescin-isothiocyanate (FITC) conjugated CD80, CD86, $K^d$, I-$A^d$, phycoerythrin (PE) conjugated CD11c and APC conjugated CD11b are used to stain cells. One to three×$10^6$ cells are used for individual stains. Non-specific binding is blocked by incubating cells with blocking buffer (PBS, 10% FBS, 20 ug/ml 2.4G2). After blocking, cells are incubated with the primary antibodies for 20 minutes. Unless specified, all antibodies are used at 1 ug/ml in a volume of 100 ul. Cells are washed once with PBS and resuspended in PBS before being acquired using the flow cytometer. Data is analyzed using the Cellquest Software (BD biosciences).

For the APC assay, female DO11.10 transgenic mice are euthanized. Spleens are isolated from mice and red blood cells lysed using ACK lysis buffer as mentioned above. Cells are resuspended in DMEM media and plated at the indicated concentration (refer to Figures) in 96-well plates in triplicate in a total volume of 100 ul/well. DCs isolated are washed once in DMEM media and pulsed with 1 uM OVA323-334 peptide for 1 hour at 37° C. in incubator or water bath. After one hour, cells are washed twice with complete DMEM media. Cells are then plated at a concentration of 0.25 and $10^6$ cells/well in a volume of 100 ul along with the already plated DO11.10 spleen cells. The 96-well plate is incubated at 37° C. in incubator, 5% $CO_2$. On the 3$^{rd}$ day after start of culture, 1 uCi of 3H-thymidine is added to each well in a volume of 25 ul/well. The plates are harvested using a standard cell harvester 16 hours after addition of 3H-thymidine and the counts analyzed using a scintillation counter. Data is analyzed and graphs plotted using Excel software (Microsoft Corporation, Seattle, Wash.).

C. Study Results

As specified above, DCs cultured with GM-CSF alone or GM-CSF+IL-15 induced efficient proliferation of antigen specific DO11.10 T cells. In contrast, DCs cultures with GM-CSF+IL-21 did not induce good proliferation of DO11.10 T cells. In keeping with this data, DCs cultures with flt3L+IL-21 also did not induce good proliferation of DO11.10 cells in contrast to the efficient proliferation seen with DCs cultured with flt3L alone. Dendritic cells cultured in GM-CSF+IL-21 express lower levels of MHC Class II molecules and higher levels of MHC Class I molecules than DCs cultured with GM-CSF alone, suggesting that this is be a mechanism by which IL-21 inhibits DC mediated T cell function.

Example 2

IL-21 Inhibits DTH at the Challenge Phase but not the Sensitization Phase

A. Summary

DTH responses are classic immune responses that are initiated by CD4+ T cells and mediated by T cells, neutrophils and macrophages. A DTH response is a good indicator of a CD4+ T cell mediated response. Mice are immunized sub-cutaneously with chicken ovalbumin protein (OVA) in either of 2 adjuvants, RIBI or CFA. This phase is called the sensitization phase (days 0-6). Ear measurements are taken seven days later. Mice are then injected in the ear with control PBS (left ear) or OVA (right ear). This phase is called the challenge phase (days 7-8). Immune responses generated to OVA induce inflammation in the ear resulting an increase in ear thickness in 24 hours in the OVA-treated, but not in the PBS-treated ear. This is measured using calipers. A DTH experiment is done as specified above. Groups of mice are injected intra-peritoneally with a single injection/day of PBS or IL-21 from either days 0-6 (sensitization phase) or days 7-8 (challenge phase). Mice treated with IL-21 from days 0-6 show normal immune responses as shown by an increase in ear thickness compared to PBS treated mice. In contrast, mice treated with IL-21 from days 7-8 show a decreased thickening of ear in 24 hours in the OVA-treated, but not in the PBS-treated ear.

B. Study Design

C57BL6 mice (n=8/group) are immunized in the back with 100 μg chicken ovalbumin (OVA) emulsified in RIBI adjuvant (Corixa, Seattle, Wash.) in a total volume of 200 μl. A 0.5 mg/ml of ovalbumin is added to a single vial of RIBI and vortexed vigorously for 2 minutes to form an emulsion that is used to inject mice. Seven days after the immunization, mice are injected with 10 μl PBS in the left ear (control) and with 10 μg OVA in PBS in the right ear in a volume of 10 μl. Ear thickness of all mice is measured before injecting mice in the ear (0 measurement). Ear thickness is measured 24 hours after challenge. The difference in ear thickness between the 0 measurement and the 24 hour measurement is calculated and is reflective of the inflammation in the ear. Groups of mice are injected with PBS or different concentration of IL-21 (as specified in the figures) intra-peritoneally from either days 0-6 (sensitization phase) or from days 7-8 (challenge phase). The injection on day 7 and 8 is given 2 hours before measuring ear thickness at the 0 and 24 hour time points. At the end of the 24 hour period, once ear thickness was measured, the ears were cut and placed in formalin for histological analysis.

C. Study Results and Conclusion

At 24 hour post challenge, control mice and mice treated with IL-21 from days 0-6 showed a substantial increase in ear thickness. In contrast, mice treated with IL-21 on days 7-8 showed an increase that was at least 50% less than the thickness seen in the control mice. This difference was statistically significant (p=0.0164). This suggests that IL-21 does play an important role in T cell responses and DTH at the challenge phase. In the follow-up experiment, low doses of 1L-21 (5 μg/mouse) did not have substantial effects on the DTH whereas doses from 25 μg-200 μg/mouse had a statistically significant inhibitory effect on ear thickness and therefore DTH. These data demonstrate that the effect of IL-21 is dose dependent and that IL-21 is capable of inhibiting an ongoing immune response.

Example 3

IL-21 Delays Onset of Disease in a Mouse Model for Multiple Sclerosis

A. Summary

To test if IL-21 had any effects on multiple sclerosis, the ablility of IL-21 to inhibit experimental autoimmune encephalomyelitis (EAE), a mouse model for MS was tested. The well characterized myelin oligodendrocyte glycoprotein (MOG) 35-55 peptide immunization model in C57BL/6 mice was used. The experiment was run to determine that IL-21 could delay and/or inhibit disease scores in EAE either by inhibiting DC mediated antigen presentation (as shown above) or by enhancing CD8 T cell responses. Absence of efficient CD8 T cell responses in this model exacerbates EAE (Malipiero et. al., *Eur. J. Immunol.*, 27:3151-3160, 1997). IL-21 delayed onset of disease in the EAE model in a dose dependent manner, suggesting that use of IL-21 may be beneficial in MS.

B. Study Design

Experimental autoimmune encephalomyelitis (EAE) is a mouse model for MS. In one such model, C57BL/6 mice are immunized with 100 μg MOG peptide (MOG35-55) emulsified in RIBI adjuvant. Two milliliters of a 0.5 mg/ml preparation of the MOG35-55 in PBS is added to a vial of RIBI and vortexed vigorously to emulsify the solution. The backs of mice are shaved and 100 μg MOG/RIBI is injected s.c in the backs of mice. Weights of mice are taken 2 days before and every day after the immunization. Mice are then injected on day 2 i.v with 200 μl pertussis toxin (PT), a final concentration of 200 ng/mouse. Mice are monitored daily for clinical scores. Groups of mice are injected i.p. with 200 μl PBS, 100 μg BSA, 10 μg or 100 μg IL-21 in a 200 μl volume from days 0-20. The weights of mice, clinical scores and incidence are evaluated and plotted for analysis.

C. Results and Conclusion

Administration of IL-21 from days 0-20 delayed onset of disease in this model in a dose dependent manner. The 100 μg IL-21 dose had a more delayed response than the 10 μg dose, providing evidence that IL-21 is able to inhibit autoimmunity.

Example 4

IL-21 Cultured DCs in EAE

A. Summary

As specified in Example 1, dendritic cells generated in the presence of IL-21 are poor antigen presenting cell in vitro and in vivo, suggesting that IL-21 can enhance tolerogenic capacity of DCs. We wanted to see if these IL-21 DCs can inhibit EAE in the above described MOG35-55 model. DCs cultured with GM-CSF alone or GM-CSF+IL-21 are pulsed with MOG35-55 peptide and injected s.c into C57BL/6 mice. Clinical scores and weight loss are monitored to study the effects of IL-21 DCs compared to control DCs. Delay in onset or decreased clinical scores indicates tolerogenic potential of IL-21 DCs compared to control DCs.

B. Study Design

Female C57BL/6 mice, approximately 8-10 weeks of age are euthanized. The femurs from these mice are isolated and crushed using a mortar and pestle to extract marrow cells. Red blood cells are lysed by incubating cells for 2 minutes with ACK lysis buffer (0.15M $NH_4Cl$, 1 mM $KHCO_3$, 0.1 mM EDTA) followed by neutralization with RPMI-10 media (RPMI with 10% FBS). The cells are washed once with RPMI-10 media and cultured at 2 million cells/ml in 24 well plates in complete DMEM media in a total volume of 3 ml/well with the indicated cytokines. Cells are cultured with 20 ng/ml recombinant murine GM-CSF (rmGM-CSF, R & D systems) or rmGM-CSF+30 ng/ml recombinant murine IL-15 (mIL-15, R & D systems) or rmGM-CSF+30 ng/ml) recombinant murine IL-21. Cells are refed with fresh media and cytokines every 4 days. On day 10 after start of culture, cells are harvested and pulsed with 1 μM MOG35-55 peptide for 1 hr at 37° C. Cells are washed twice with PBS, resuspended in PBS and injected s.c into the footpads of C57BL/6 mice ($1 \times 10^6$ cells/mouse). Weights of mice are taken 2 days before and every day after the immunization. Mice are then injected on day 2 i.v with 200 μl pertussis toxin (PT), a final concentration of 200 ng/mouse. Mice are monitored daily for clinical scores. The weights of mice, clinical scores and incidence are evaluated and plotted for analysis.

C. Results and Conlcusion

Ability of IL-21 DCs to delay onset of disease and/or decrease incidence or clinical severity can show that IL21 DCs induce tolerogenic potential and inhibit autoimmune disease.

Example 5

1L-21 in DSS Colitis

A. Summary

DSS colitis is one of the many mouse models for human IBD. Oral administration of dextran sodium sulfate (DSS) to mice results in weight loss and diarrhea over a period of 5-8 days. Removal of DSS after 7 days results in slow recovery in weight loss, as well as, re-epithelialization of the colon. IL-21 is administered to mice concurrently with DSS treatment and the effect of IL-21 on weight loss and Disease Activity Index (DAI) scores followed from days 0-13. Inhibition of weight loss and DAI scores indicates that IL-21 inhibits colitis.

B. Study Design

Groups of C57BL/6 mice (n=6/gp) are fed 2% or 3% DSS in water from days 0-7, followed by water from days 8-13. IL-21 is administered i.p. from days 0-8 at doses ranging from 10 ug-100 ug/mouse. During the course of the DSS administration, mice are monitored for weight loss and DAI scores. DAI scores involves 3 parameters—a sum of fecal consistency score, hemoccult score in feces and histological score of the colon at the time of sacrifice. Mice are sacrificed at days 8 and days 13. Length of colons and histological scores are evaluated.

C. Results and Conclusions

Ability of IL-21 to inhibit weight loss and/or DAI scores is a reflection of IL-21 ability to inhibit colitis in this model, suggesting that IL-21 is useful for treatment of human IBD.

Example 6

IL-21 in TNBS Colitis

A. Summary

TNBS colitis is one of the many mouse models for human IBD. Rectal administration of 2-4-6 trinitrobenzene sulfonic acid (TNBS) to mice results in diarrhea and intestinal inflammation over a period of 10-14 days. IL-21 is administered to mice concurrently with TNBS treatment and the effect of IL-21 on intestinal inflammation evaluated. Inhibition of inflammation indicates that IL-21 inhibits colitis.

B. Study Design

Groups of BALB/c or SJL mice (n=6/gp) are treated with an intra-rectal enema of 1-2% TNBS in 30-50% Ethanol or Ethanol alone (vehicle control), on days 0 and 7. IL-21 is administered i.p. from days 0-8 at doses ranging from 10 µg-100 µg/mouse. Mice are sacrificed at days 10 and days 13. Length of colons and histological scores are evaluated.

C. Results and Conclusions

Ability of IL-21 to inhibit intestinal inflammation demonstrates the ability of IL-21 to inhibit colitis in this model, suggesting that IL-21 is useful in the treatment of human IBD.

Example 7

IL-21 in $CD4^+CD45RB^{hi}$ ($CD25^-$) Colitis and Psoriasis

A. Summary

Transfer of CD4+CD45RB$^{hi}$ or CD4+CD25-T cells into syngenic SCID mice results in colitis in the mice. Co-transfer of regulatory T cells (CD4+CD25+ or CD4+CD45RB$^{lo}$) inhibits this colitis. After transfer of CD4+CD25-T cells into mice, if mice are additionally injected with staphylococcal enterotoxin B (SEB), mice not only develop colitis, but also psoriasis. IL-21 is administered from days 0-21 after cell transfer and symptoms for colitis and psoriasis are monitored. Inhibiton of psoriatic score or colitis (histology) indicates that IL-21 can inhibit these autoimmune diseases.

B. Study Design

Spleens and inguinal lymph nodes are isolated from B10.D2 mice. Single cell suspensions are formed and counted. Using the Miltenyi Bead system, CD25+cells are sorted out by positive selection. Cells are stained with CD25-PE (BD Pharmingen) at 1:100 dilution and incubated for 15 minutes. Excess antibody is washed out and the cells are incubated with 10 ul anti-PE beads/$10^6$ cells for 20 minutes. The cells are washed with PBS and passed over an LS column (Miltenyi Biotech). Cells that pass through the column (CD25−) are retained for further analysis. A CD4 enrichment cocktail (Stem Cell technologies) is added (1:100) to these CD25-cells and incubated for 15 minutes. Cells are washed with PBS. A 1:10 dilution of anti-biotin tetramer is added to the cells for 15 minutes followed by a magnetic colloid (60 ul/$10^6$ cells) for 15 minutes (all from Stem Cell Technologies). Cells are passed through a negative selection column (0.5", Stem cell Technologies). Cells that pass through are the CD4+CD25− cells. Purity is analyzed using flow cytometry. $0.4\times10^6$ cells are injected i.v into naïve CB-17 SCID mice in a total volume of 200 µl. Mice are injected i.p with 10 µg SEB the following day (d1). Symptoms for psoriasis and colitis are followed from 2-5 weeks. Groups of mice are injected i.p. with PBS, 100 µg BSA or 10-100 µg IL-21 from days 1-20.

C. Results and Conclusion

Inhibiton of psoriatic and colitis symptoms in IL-21 treated mice indicates that IL-21 can inhbit autoimmune symptoms in this model for psoriasis and colitis.

Example 8

IL-21 in Contact Hypersensitivity

A. Summary

Contact hypersensitivity can be induced in mice using a variety of contact allergens including dinitrofluorobenzene (DNFB) and oxazolone. Mice are sensitized topically with the allergen in a vehicle of acetone and olive oil and then challenged in the ear with the allergen in olive oil alone. Change in ear thickness is a measure of the immune response against the allergen. IL-21 is administered either at the sensitization phase (d0-5) or during the challenge phase (d5-6). Inhibition of ear thickness by IL-21 indicates a role for IL-21 in inhibiting contact hypersensitivity.

B. Study Design

C57B1/6 mice are painted in the back with 0.5% DNFB in acetone:olive oil (4:1) or acetone:olive oil alone on d0. On d5, ear thickness of mice is measured using calipers and mice are challenged in the ears with olive oil alone (control) or 0.25% DNFB in olive oil by dropping a 25 µl solution onto the ear. Change in ear thickness is measured on d6 and the inflammation calculated as a difference in ear thickness between d5 and d6. Groups of mice are injected i.p. with PBS or 10-100 μg IL-21 on either days 0-5 or days 5-6.

C. Results and Conclusion

Inhibition of ear thickness by IL-21 demonstrates that IL-21 can be useful in inhibiting contact hypersensitivity.

Example 9

Use of IL-21 to Treat Systemic Lupus Erythematosus

A. Summary

The mouse model for lupus is a spontaneous model in female NZBWF1 mice. The mice develop proteinuria starting about 20-25 weeks of age followed by anti-ds DNA antibodies, both signs of autoimmunity. IL-21 is administered 3×/week for 5 weeks starting week 20. Proteinuria and anti-ds DNA antibodies are detected in the urine and blood of mice at varying time points. Decrease in proteinuria and anti-ds DNA antibodies in IL-21 treated mice is indicative of an inhibitory effect of IL-21 in a mouse lupus model (Gross et. al., *Nature* 404:995-999, 2000).

B. Study Design

Female NZBWF1 mice (n=15/gp) are tested for proteinuria and anti-ds DNA antibodies in urine and blood respectively starting week 15 (once a week). Groups of mice are treated with PBS alone or 10-100 μg IL-21 3X/week for 5 weeks starting week 20. Protenuria and blood anti-ds DNA antibody titers are measured by standard assays 1X/week.

C. Results and Conclusion:

A decrease in proteinuria and anti-ds DNA antibodies in IL-21-treated mice is indicative that IL-21 has an inhibitory effect in a mouse lupus model.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of decreasing a CD4+ T-cell autoimmune response in a mammal comprising administering a therapeutically effective amount of a pharmaceutical composition comprising an IL-21 polypeptide as shown in SEQ ID NO:2 from amino acid residue 30 to 162, in a pharmaceutically acceptable vehicle.

2. The method of claim 1, wherein the CD4+ T cell-mediated immune response is decreased in the diseases selected from the group consisting of psoriasis, atopic dermatitis and systemic lupus erythematosus.

3. The method of claim 1, wherein treatment results in delayed onset of disease.

4. The method of claim 1 wherein the mammal is a human.

5. A method of treating a mammal with multiple sclerosis comprising administering a therapeutically effective amount of a pharmaceutical composition comprising an IL-21 polypeptide as shown in SEQ ID NO:2 from amino acid residue 30 to 162, in a pharmaceutically acceptable vehicle.

6. The method of claims 5, wherein treatment results in a reduction in severity of disease.

7. The method of claims 1 or 5, wherein the mammal is a human.

* * * * *

SEQUENCE LISTING

<160> NUMBER OF SEQ ID NOS: 10

<210> SEQ ID NO 1
<211> LENGTH: 642
<212> TYPE: DNA
<213> ORGANISM: Homo sapiens
<220> FEATURE:
<221> NAME/KEY: CDS
<222> LOCATION: (47)...(532)

<400> SEQUENCE: 1

```
gctgaagtga aaacgagacc aaggtctagc tctactgttg gtactt atg aga tcc        55
                                                  Met Arg Ser
                                                    1 agt cct ggc aac atg gag agg att gtc atc tgt ctg atg gtc atc ttc      103
Ser Pro Gly Asn Met Glu Arg Ile Val Ile Cys Leu Met Val Ile Phe
  5              10                  15 ttg ggg aca ctg gtc cac aaa tca agc tcc caa ggt caa gat cgc cac      151
Leu Gly Thr Leu Val His Lys Ser Ser Ser Gln Gly Gln Asp Arg His
 20                  25                  30                  35 atg att aga atg cgt caa ctt ata gat att gtt gat cag ctg aaa aat      199
Met Ile Arg Met Arg Gln Leu Ile Asp Ile Val Asp Gln Leu Lys Asn
                 40                  45                  50 tat gtg aat gac ttg gtc cct gaa ttt ctg cca gct cca gaa gat gta      247
Tyr Val Asn Asp Leu Val Pro Glu Phe Leu Pro Ala Pro Glu Asp Val
             55                  60                  65 gag aca aac tgt gag tgg tca gct ttt tcc tgt ttt cag aag gcc caa      295
Glu Thr Asn Cys Glu Trp Ser Ala Phe Ser Cys Phe Gln Lys Ala Gln
         70                  75                  80 cta aag tca gca aat aca gga aac aat gaa agg ata atc aat gta tca      343
Leu Lys Ser Ala Asn Thr Gly Asn Asn Glu Arg Ile Ile Asn Val Ser
 85                  90                  95 att aaa aag ctg aag agg aaa cca cct tcc aca aat gca ggg aga aga      391
Ile Lys Lys Leu Lys Arg Lys Pro Pro Ser Thr Asn Ala Gly Arg Arg
100                 105                 110                 115 cag aaa cac aga cta aca tgc cct tca tgt gat tct tat gag aaa aaa      439
Gln Lys His Arg Leu Thr Cys Pro Ser Cys Asp Ser Tyr Glu Lys Lys
                120                 125                 130 cca ccc aaa gaa ttc cta gaa aga ttc aaa tca ctt ctc caa aag atg      487
Pro Pro Lys Glu Phe Leu Glu Arg Phe Lys Ser Leu Leu Gln Lys Met
            135                 140                 145
```

```
att cat cag cat ctg tcc tct aga aca cac gga agt gaa gat tcc      532
Ile His Gln His Leu Ser Ser Arg Thr His Gly Ser Glu Asp Ser
        150                 155                 160 tgaggatcta acttgcagtt ggacactatg ttacatactc taatatagta gtgaaagtca    592
tttctttgta ttccaagtgg aggagcccta ttaaattata taaagaaata              642

<210> SEQ ID NO 2
<211> LENGTH: 162
<212> TYPE: PRT
<213> ORGANISM: Homo sapiens

<400> SEQUENCE: 2

Met Arg Ser Ser Pro Gly Asn Met Glu Arg Ile Val Ile Cys Leu Met
 1               5                  10                  15

Val Ile Phe Leu Gly Thr Leu Val His Lys Ser Ser Gln Gly Gln
             20                  25                  30

Asp Arg His Met Ile Arg Met Arg Gln Leu Ile Asp Ile Val Asp Gln
         35                  40                  45

Leu Lys Asn Tyr Val Asn Asp Leu Val Pro Glu Phe Leu Pro Ala Pro
 50                  55                  60

Glu Asp Val Glu Thr Asn Cys Glu Trp Ser Ala Phe Ser Cys Phe Gln
 65                  70                  75                  80

Lys Ala Gln Leu Lys Ser Ala Asn Thr Gly Asn Asn Glu Arg Ile Ile
                 85                  90                  95

Asn Val Ser Ile Lys Lys Leu Lys Arg Lys Pro Pro Ser Thr Asn Ala
                100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
        130                 135                 140

Gln Lys Met Ile His Gln His Leu Ser Ser Arg Thr His Gly Ser Glu
145                 150                 155                 160

Asp Ser

<210> SEQ ID NO 3
<211> LENGTH: 3072
<212> TYPE: DNA
<213> ORGANISM: Homo sapiens
<220> FEATURE:
<221> NAME/KEY: CDS
<222> LOCATION: (54)...(491)

<400> SEQUENCE: 3
gagaaccaga ccaaggccct gtcatcagct cctggagact cagttctggt ggc atg      56
                                                            Met
                                                             1 gag agg acc ctt gtc tgt ctg gta gtc atc ttc ttg ggg aca gtg gcc    104
Glu Arg Thr Leu Val Cys Leu Val Val Ile Phe Leu Gly Thr Val Ala
         5                  10                  15 cat aaa tca agc ccc caa ggg cca gat cgc ctc ctg att aga ctt cgt    152
His Lys Ser Ser Pro Gln Gly Pro Asp Arg Leu Leu Ile Arg Leu Arg
             20                  25                  30 cac ctt att gac att gtt gaa cag ctg aaa atc tat gaa aat gac ttg    200
His Leu Ile Asp Ile Val Glu Gln Leu Lys Ile Tyr Glu Asn Asp Leu
         35                  40                  45 gat cct gaa ctt cta tca gct cca caa gat gta aag ggg cac tgt gag    248
Asp Pro Glu Leu Leu Ser Ala Pro Gln Asp Val Lys Gly His Cys Glu
 50                  55                  60                  65
```

```
cat gca gct ttt gcc tgt ttt cag aag gcc aaa ctc aag cca tca aac         296
His Ala Ala Phe Ala Cys Phe Gln Lys Ala Lys Leu Lys Pro Ser Asn
                 70                  75                  80 cct gga aac aat aag aca ttc atc att gac ctc gtg gcc cag ctc agg         344
Pro Gly Asn Asn Lys Thr Phe Ile Ile Asp Leu Val Ala Gln Leu Arg
             85                  90                  95 agg agg ctg cct gcc agg agg gga gga aag aaa cag aag cac ata gct         392
Arg Arg Leu Pro Ala Arg Arg Gly Gly Lys Lys Gln Lys His Ile Ala
        100                 105                 110 aaa tgc cct tcc tgt gat tcg tat gag aaa agg aca ccc aaa gaa ttc         440
Lys Cys Pro Ser Cys Asp Ser Tyr Glu Lys Arg Thr Pro Lys Glu Phe
    115                 120                 125 cta gaa aga cta aaa tgg ctc ctt caa aag atg att cat cag cat ctc         488
Leu Glu Arg Leu Lys Trp Leu Leu Gln Lys Met Ile His Gln His Leu
130                 135                 140                 145 tcc tagaacacat aggacccgaa gattcctgag gatccgagaa gattcccgag              541
Ser gactgaggag acgccggaca ctatagacgc tcacgaatgc aggagtacat cttgcctctt       601
gggattgcaa gtggagaagt acgatacgtt atgataagaa caactcagaa aagctatagg       661
ttaagatcct ttcgcccatt aactaagcag acattgtggt tccctgcaca gactccatgc       721
tgtcaacatg gaaaatctca actcaacaag agcccagctt cccgtgtcag ggatttctgg       781
tgcttctcaa gctgtggctt catcttattg cccaactgtg acattctttg attggaaggg       841
gaaaactaaa gcttttagca aaatacagc tagggaattt gtcgatctgc gagagtaaga       901
cctcttatga tcctaacgga atgatgtaag ctggaaataa taagcataag atgaaattga      961
aaattgaagt ctttattctt taagaaaaac tttgtacttg aaagcatgtc tgaagagttt     1021
actcattacc acaaacatct agcatattga taactaacat ctttatactc tacaagagag     1081
gctttccaga taggtacagt ttttcttctc tattaggtct atcaaaattt aacctattat     1141
gagggtcacc cctggctttc actgttttt taaagaggca agggtgtagt aagaagcagg     1201
cttaagttgc cttcctccca atgtcaagtt cctttataag ctaatagttt aatcttgtga     1261
agatggcaat gaaagcctgt ggaagtgcaa acctcactat cttctggagc caagtagaat     1321
tttcaagttt gtagctctca cctcaagtgg ttatgggtgt cctgtgatga atctgctagc     1381
tccagcctca gtctcctctc ccacatcctt tcctttcttt cctctttgaa acttctaaga     1441
aaaagcaatc caaacaagtt cagcacttaa gacacattgc atgcacactt ttgataagtt     1501
aaatccaacc atctatttaa aatcaaaatc aggagatgag ccaagagacc agaggttctg     1561
ttccagtttt aaacagactt ttactgaaca tcccaatctt ttaaccacag aggctaaatt     1621
gagcaaatag ttttgccatt tgatataatt tccaacagta tgtttcaatg tcaagttaaa     1681
aagtctacaa agctattttc cctggagtgg tatcatcgct ttgagaattt cttatggtta     1741
aaatggatct gagatccaag catggcctgg gggatggttt tgatctaagg aaaaaggtgt     1801
ctgtacctca cagtgccttt aaaacaagca gagatcccgt gtaccgccct aagatagcac     1861
agactagtgt taactgattc ccagaaaagt gtcacaatca gaaccaacgc attctcttaa     1921
actttaaaaa tatgtattgc aaagaacttg tgtaactgta aatgtgtgac tgttgatgac     1981
attatacaca catagcccac gtaagtgtcc aatggtgcta gcattggttg ctgagtttgc     2041
tgctcgaaag ctgaagcaga gatgcagtcc ttcacaaagc aatgatggac agagagggga     2101
gtctccatgt tttattcttt tgttgttct ggctgtgtaa ctgttgactt cttgacattg     2161 tgattttat atttaagaca atgtatttat tttggtgtgt ttattgttct agcctttaa      2221
```

```
atcactgaca atttctaatc aagaagtaca aataattcaa tgcagcacag gctaagagct    2281
tgtatcgttt ggaaaagcca gtgaaggctt ctccactagc catgggaaag ctacgcttta    2341
gagtaaacta gacaaaattg cacagcagtc ttgaacctct ctgtgctcaa gactcagcca    2401
gtcctttgac attattgttc actgtgggtg ggaacacatt ggacctgaca cactgttgtg    2461
tgtccatgaa ggttgccact ggtgtaagct ttttttggtt ttcattctct tatctgtaga    2521
acaagaatgt ggggctttcc taagtctatt ctgtatttta ttctgaactt cgtatgtctg    2581
agttttaatg ttttgagtac tcttacagga acacctgacc acactttga gttaaatttt     2641 atcccaagtg tgatatttag ttgttcaaaa agggaaggga tatacataca tacatacata    2701
catacataca tatatatata tatatataca tatatatata tatatatatg tatatatata    2761
tatatataga gagagagaga gagagagaga gagaaagaga gagaggttgt tgtaggtcat    2821
aggagttcag aggaaatcag ttatggccgt taatactgta gctgaaagtg ttttctttgt    2881
gaataaattc atagcattat tgatctatgt tattgctctg ttttatttac agtcacacct    2941
gagaatttag ttttaatatg aatgatgtac tttataactt aatgattatt tattatgtat    3001
ttggttttga atgtttgtgt tcatggcttc ttatttaaga cctgatcata ttaaatgcta    3061
cccagtccgg a    3072
```

<210> SEQ ID NO 4
<211> LENGTH: 146
<212> TYPE: PRT
<213> ORGANISM: Homo sapiens

<400> SEQUENCE: 4

```
Met Glu Arg Thr Leu Val Cys Leu Val Val Ile Phe Leu Gly Thr Val
  1               5                  10                  15

Ala His Lys Ser Ser Pro Gln Gly Pro Asp Arg Leu Leu Ile Arg Leu
             20                  25                  30

Arg His Leu Ile Asp Ile Val Glu Gln Leu Lys Ile Tyr Glu Asn Asp
         35                  40                  45

Leu Asp Pro Glu Leu Leu Ser Ala Pro Gln Asp Val Lys Gly His Cys
     50                  55                  60

Glu His Ala Ala Phe Ala Cys Phe Gln Lys Ala Lys Leu Lys Pro Ser
 65                  70                  75                  80

Asn Pro Gly Asn Asn Lys Thr Phe Ile Ile Asp Leu Val Ala Gln Leu
                 85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
    130                 135                 140

Leu Ser
145
```

<210> SEQ ID NO 5
<211> LENGTH: 153
<212> TYPE: PRT
<213> ORGANISM: Homo sapiens

<400> SEQUENCE: 5

```
Met Tyr Arg Met Gln Leu Leu Ser Cys Ile Ala Leu Ser Leu Ala Leu
  1               5                  10                  15
```

Val Thr Asn Ser Ala Pro Thr Ser Ser Thr Lys Lys Thr Gln Leu
        20                  25                  30

Gln Leu Glu His Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 6
<211> LENGTH: 153
<212> TYPE: PRT
<213> ORGANISM: Homo sapiens

<400> SEQUENCE: 6

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
            35                  40                  45

Thr Glu Leu Thr Val Thr Asp Ile Phe Ala Ala Ser Lys Asn Thr Thr
50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
            115                 120                 125

Asn Gln Ser Thr Leu Glu Asn Phe Leu Glu Arg Leu Lys Thr Ile Met
130                 135                 140

Arg Glu Lys Tyr Ser Lys Cys Ser Ser
145                 150

<210> SEQ ID NO 7
<211> LENGTH: 162
<212> TYPE: PRT
<213> ORGANISM: Homo sapiens

<400> SEQUENCE: 7

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

-continued

```
Val Phe Ile Leu Gly Cys Phe Ser Ala Gly Leu Pro Lys Thr Glu Ala
             35                  40                  45
Asn Trp Val Asn Val Ile Ser Asp Leu Lys Lys Ile Glu Asp Leu Ile
 50                  55                  60
Gln Ser Met His Ile Asp Ala Thr Leu Tyr Thr Glu Ser Asp Val His
 65                  70                  75                  80
Pro Ser Cys Lys Val Thr Ala Met Lys Cys Phe Leu Leu Glu Leu Gln
                 85                  90                  95
Val Ile Ser Leu Glu Ser Gly Asp Ala Ser Ile His Asp Thr Val Glu
            100                 105                 110
Asn Leu Ile Ile Leu Ala Asn Asn Ser Leu Ser Ser Asn Gly Asn Val
            115                 120                 125
Thr Glu Ser Gly Cys Lys Glu Cys Glu Glu Leu Glu Glu Lys Asn Ile
130                 135                 140
Lys Glu Phe Leu Gln Ser Phe Val His Ile Val Gln Met Phe Ile Asn
145                 150                 155                 160
Thr Ser
```

<210> SEQ ID NO 8
<211> LENGTH: 144
<212> TYPE: PRT
<213> ORGANISM: Homo sapiens

<400> SEQUENCE: 8

```
Met Trp Leu Gln Ser Leu Leu Leu Leu Gly Thr Val Ala Cys Ser Ile
  1               5                  10                  15
Ser Ala Pro Ala Arg Ser Pro Ser Pro Ser Thr Gln Pro Trp Glu His
             20                  25                  30
Val Asn Ala Ile Gln Glu Ala Arg Arg Leu Leu Asn Leu Ser Arg Asp
             35                  40                  45
Thr Ala Ala Glu Met Asn Glu Thr Val Glu Val Ile Ser Glu Met Phe
 50                  55                  60
Asp Leu Gln Glu Pro Thr Cys Leu Gln Thr Arg Leu Glu Leu Tyr Lys
 65                  70                  75                  80
Gln Gly Leu Arg Gly Ser Leu Thr Lys Leu Lys Gly Pro Leu Thr Met
                 85                  90                  95
Met Ala Ser His Tyr Lys Gln His Cys Pro Pro Thr Pro Glu Thr Ser
            100                 105                 110
Cys Ala Thr Gln Ile Ile Thr Phe Glu Ser Phe Lys Glu Asn Leu Lys
            115                 120                 125
Asp Phe Leu Leu Val Ile Pro Phe Asp Cys Trp Glu Pro Val Gln Glu
130                 135                 140
```

<210> SEQ ID NO 9
<211> LENGTH: 1614
<212> TYPE: DNA
<213> ORGANISM: Homo sapiens
<220> FEATURE:
<221> NAME/KEY: CDS
<222> LOCATION: (1)...(1614)

<400> SEQUENCE: 9

```
atg ccg cgt ggc tgg gcc gcc ccc ttg ctc ctg ctg ctg ctc cag gga        48
Met Pro Arg Gly Trp Ala Ala Pro Leu Leu Leu Leu Leu Leu Gln Gly
  1               5                  10                  15 ggc tgg ggc tgc ccc gac ctc gtc tgc tac acc gat tac ctc cag acg        96
Gly Trp Gly Cys Pro Asp Leu Val Cys Tyr Thr Asp Tyr Leu Gln Thr
```

```
                20                  25                  30
gtc atc tgc atc ctg gaa atg tgg aac ctc cac ccc agc acg ctc acc     144
Val Ile Cys Ile Leu Glu Met Trp Asn Leu His Pro Ser Thr Leu Thr
         35                  40                  45 ctt acc tgg caa gac cag tat gaa gag ctg aag gac gag gcc acc tcc     192
Leu Thr Trp Gln Asp Gln Tyr Glu Glu Leu Lys Asp Glu Ala Thr Ser
 50                  55                  60 tgc agc ctc cac agg tcg gcc cac aat gcc acg cat gcc acc tac acc     240
Cys Ser Leu His Arg Ser Ala His Asn Ala Thr His Ala Thr Tyr Thr
 65                  70                  75                  80 tgc cac atg gat gta ttc cac ttc atg gcc gac gac att ttc agt gtc     288
Cys His Met Asp Val Phe His Phe Met Ala Asp Asp Ile Phe Ser Val
                 85                  90                  95 aac atc aca gac cag tct ggc aac tac tcc cag gag tgt ggc agc ttt     336
Asn Ile Thr Asp Gln Ser Gly Asn Tyr Ser Gln Glu Cys Gly Ser Phe
            100                 105                 110 ctc ctg gct gag agc atc aag ccg gct ccc cct ttc aac gtg act gtg     384
Leu Leu Ala Glu Ser Ile Lys Pro Ala Pro Pro Phe Asn Val Thr Val
        115                 120                 125 acc ttc tca gga cag tat aat atc tcc tgg cgc tca gat tac gaa gac     432
Thr Phe Ser Gly Gln Tyr Asn Ile Ser Trp Arg Ser Asp Tyr Glu Asp
    130                 135                 140 cct gcc ttc tac atg ctg aag ggc aag ctt cag tat gag ctg cag tac     480
Pro Ala Phe Tyr Met Leu Lys Gly Lys Leu Gln Tyr Glu Leu Gln Tyr
145                 150                 155                 160 agg aac cgg gga gac ccc tgg gct gtg agt ccg agg aga aag ctg atc     528
Arg Asn Arg Gly Asp Pro Trp Ala Val Ser Pro Arg Arg Lys Leu Ile
                165                 170                 175 tca gtg gac tca aga agt gtc tcc ctc ctc ccc ctg gag ttc cgc aaa     576
Ser Val Asp Ser Arg Ser Val Ser Leu Leu Pro Leu Glu Phe Arg Lys
            180                 185                 190 gac tcg agc tat gag ctg cag gtg cgg gca ggg ccc atg cct ggc tcc     624
Asp Ser Ser Tyr Glu Leu Gln Val Arg Ala Gly Pro Met Pro Gly Ser
        195                 200                 205 tcc tac cag ggg acc tgg agt gaa tgg agt gac ccg gtc atc ttt cag     672
Ser Tyr Gln Gly Thr Trp Ser Glu Trp Ser Asp Pro Val Ile Phe Gln
    210                 215                 220 acc cag tca gag gag tta aag gaa ggc tgg aac cct cac ctg ctg ctt     720
Thr Gln Ser Glu Glu Leu Lys Glu Gly Trp Asn Pro His Leu Leu Leu
225                 230                 235                 240 ctc ctc ctg ctt gtc ata gtc ttc att cct gcc ttc tgg agc ctg aag     768
Leu Leu Leu Leu Val Ile Val Phe Ile Pro Ala Phe Trp Ser Leu Lys
                245                 250                 255 acc cat cca ttg tgg agg cta tgg aag aag ata tgg gcc gtc ccc agc     816
Thr His Pro Leu Trp Arg Leu Trp Lys Lys Ile Trp Ala Val Pro Ser
            260                 265                 270 cct gag cgg ttc ttc atg ccc ctg tac aag ggc tgc agc gga gac ttc     864
Pro Glu Arg Phe Phe Met Pro Leu Tyr Lys Gly Cys Ser Gly Asp Phe
        275                 280                 285 aag aaa tgg gtg ggt gca ccc ttc act ggc tcc agc ctg gag ctg gga     912
Lys Lys Trp Val Gly Ala Pro Phe Thr Gly Ser Ser Leu Glu Leu Gly
    290                 295                 300 ccc tgg agc cca gag gtg ccc tcc acc ctg gag gtg tac agc tgc cac     960
Pro Trp Ser Pro Glu Val Pro Ser Thr Leu Glu Val Tyr Ser Cys His
305                 310                 315                 320 cca cca cgg agc ccg gcc aag agg ctg cag ctc acg gag cta caa gaa    1008
Pro Pro Arg Ser Pro Ala Lys Arg Leu Gln Leu Thr Glu Leu Gln Glu
                325                 330                 335 cca gca gag ctg gtg gag tct gac ggt gtg ccc aag ccc agc ttc tgg    1056
```

```
                                    -continued

Pro Ala Glu Leu Val Glu Ser Asp Gly Val Pro Lys Pro Ser Phe Trp
            340                 345                 350 ccg aca gcc cag aac tcg ggg ggc tca gct tac agt gag gag agg gat      1104
Pro Thr Ala Gln Asn Ser Gly Gly Ser Ala Tyr Ser Glu Glu Arg Asp
            355                 360                 365 cgg cca tac ggc ctg gtg tcc att gac aca gtg act gtg cta gat gca      1152
Arg Pro Tyr Gly Leu Val Ser Ile Asp Thr Val Thr Val Leu Asp Ala
        370                 375                 380 gag ggg cca tgc acc tgg ccc tgc agc tgt gag gat gac ggc tac cca      1200
Glu Gly Pro Cys Thr Trp Pro Cys Ser Cys Glu Asp Asp Gly Tyr Pro
385                 390                 395                 400 gcc ctg gac ctg gat gct ggc ctg gag ccc agc cca ggc cta gag gac      1248
Ala Leu Asp Leu Asp Ala Gly Leu Glu Pro Ser Pro Gly Leu Glu Asp
            405                 410                 415 cca ctc ttg gat gca ggg acc aca gtc ctg tcc tgt ggc tgt gtc tca      1296
Pro Leu Leu Asp Ala Gly Thr Thr Val Leu Ser Cys Gly Cys Val Ser
            420                 425                 430 gct ggc agc cct ggg cta gga ggg ccc ctg gga agc ctc ctg gac aga      1344
Ala Gly Ser Pro Gly Leu Gly Gly Pro Leu Gly Ser Leu Leu Asp Arg
            435                 440                 445 cta aag cca ccc ctt gca gat ggg gag gac tgg gct ggg gga ctg ccc      1392
Leu Lys Pro Pro Leu Ala Asp Gly Glu Asp Trp Ala Gly Gly Leu Pro
        450                 455                 460 tgg ggt ggc cgg tca cct gga ggg gtc tca gag agt gag gcg ggc tca      1440
Trp Gly Gly Arg Ser Pro Gly Gly Val Ser Glu Ser Glu Ala Gly Ser
465                 470                 475                 480 ccc ctg gcc ggc ctg gat atg gac acg ttt gac agt ggc ttt gtg ggc      1488
Pro Leu Ala Gly Leu Asp Met Asp Thr Phe Asp Ser Gly Phe Val Gly
            485                 490                 495 tct gac tgc agc agc cct gtg gag tgt gac ttc acc agc ccc ggg gac      1536
Ser Asp Cys Ser Ser Pro Val Glu Cys Asp Phe Thr Ser Pro Gly Asp
            500                 505                 510 gaa gga ccc ccc cgg agc tac ctc cgc cag tgg gtg gtc att cct ccg      1584
Glu Gly Pro Pro Arg Ser Tyr Leu Arg Gln Trp Val Val Ile Pro Pro
            515                 520                 525 cca ctt tcg agc cct gga ccc cag gcc agc                              1614
Pro Leu Ser Ser Pro Gly Pro Gln Ala Ser
        530                 535

<210> SEQ ID NO 10
<211> LENGTH: 538
<212> TYPE: PRT
<213> ORGANISM: Homo sapiens

<400> SEQUENCE: 10

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110
```

```
Leu Leu Ala Glu Ser Ile Lys Pro Ala Pro Pro Phe Asn Val Thr Val
            115                 120                 125

Thr Phe Ser Gly Gln Tyr Asn Ile Ser Trp Arg Ser Asp Tyr Glu Asp
        130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
            195                 200                 205

Ser Tyr Gln Gly Thr Trp Ser Glu Trp Ser Asp Pro Val Ile Phe Gln
            210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
            245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
            290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
            325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
            355                 360                 365

Arg Pro Tyr Gly Leu Val Ser Ile Asp Thr Val Thr Val Leu Asp Ala
            370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
            405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
            435                 440                 445

Leu Lys Pro Pro Leu Ala Asp Gly Glu Asp Trp Ala Gly Gly Leu Pro
            450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
            485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
            515                 520                 525
```

```
Pro Leu Ser Ser Pro Gly Pro Gln Ala Ser
    530             535
```